US011918326B2

(12) United States Patent
Koga et al.

(10) Patent No.: US 11,918,326 B2
(45) Date of Patent: Mar. 5, 2024

(54) BLOOD PRESSURE METER

(71) Applicant: OMRON HEALTHCARE CO., LTD., Muko (JP)

(72) Inventors: Toshiaki Koga, Kyoto (JP); Toshihiko Ogura, Kyoto (JP); Jun Yamagishi, Kyoto (JP); Takuya Nagata, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 758 days.

(21) Appl. No.: 17/039,361

(22) Filed: Sep. 30, 2020

(65) Prior Publication Data

US 2021/0007616 A1  Jan. 14, 2021

Related U.S. Application Data

(63) Continuation of application No. PCT/JP2019/007721, filed on Feb. 28, 2019.

(30) Foreign Application Priority Data

Apr. 20, 2018 (JP) ................................ 2018-081749

(51) Int. Cl.
*A61B 5/021* (2006.01)
*A61B 5/00* (2006.01)
*A61B 5/022* (2006.01)

(52) U.S. Cl.
CPC .......... *A61B 5/02141* (2013.01); *A61B 5/022* (2013.01); *A61B 5/6824* (2013.01); *A61B 2562/0219* (2013.01)

(58) Field of Classification Search
CPC ......... A61B 5/02; A61B 5/6824; A61B 5/022; A61B 5/02141; A61B 2562/0219;
(Continued)

(56) References Cited

U.S. PATENT DOCUMENTS 7,316,653 B2 * 1/2008 Sano .................. A61B 5/02233
600/490
2005/0192501 A1 * 9/2005 Sano .................. A61B 5/02233
600/490

(Continued)

FOREIGN PATENT DOCUMENTS

CN  101229059 A  7/2008
JP  H02-135003 U  11/1990
(Continued)

OTHER PUBLICATIONS

Apr. 16, 2019 International Search Report Issued in International Patent Application No. PCT/JP2019/007721.
(Continued)

*Primary Examiner* — Navin Natnithithadha
(74) *Attorney, Agent, or Firm* — Oliff PLC

(57) ABSTRACT

In a sphygmomanometer of the present invention, a cuff is attached to a rotating shaft on a rear surface side opposite to a front surface side arranged facing a subject during blood pressure measurement. A swing mechanism maintains a tilt angle of a central axis of the cuff with respect to a horizontal plane at a certain standby angle in a standby state of an upper arm not being inserted into the cuff, and also allows the tilt angle of the cuff to become either larger or smaller than the standby angle by the upper arm being inserted into the cuff.

6 Claims, 21 Drawing Sheets

(58) Field of Classification Search
CPC .. A61B 5/7217; A61B 2560/0247; F16F 1/06; F16F 3/04; F16F 2230/0005
USPC .......... 600/490–499; 606/202, 203
See application file for complete search history.

(56) References Cited

U.S. PATENT DOCUMENTS

| | | |
|---|---|---|
| 2008/0146950 A1 | 6/2008 | Fumuro et al. |
| 2010/0249615 A1 | 9/2010 | Kukita et al. |
| 2011/0130667 A1* | 6/2011 | Inoue .................. A61B 5/7445 600/490 |
| 2011/0245694 A1* | 10/2011 | Kukita ............... A61B 5/02233 600/490 |
| 2012/0123281 A1 | 5/2012 | Ashida |

FOREIGN PATENT DOCUMENTS

| | | |
|---|---|---|
| JP | 2008-148765 A | 7/2008 |
| JP | 2009-112521 A | 5/2009 |
| JP | 2010-136924 A | 6/2010 |
| JP | 2011-24725 A | 2/2011 |
| JP | 2016-198376 A | 12/2016 |

OTHER PUBLICATIONS

Sep. 28, 2023 Office Action issued in Chinese Patent Application No. 201980025978.4.

* cited by examiner

FIG.10  LARGE BODY SIZE

SMALL BODY SIZE

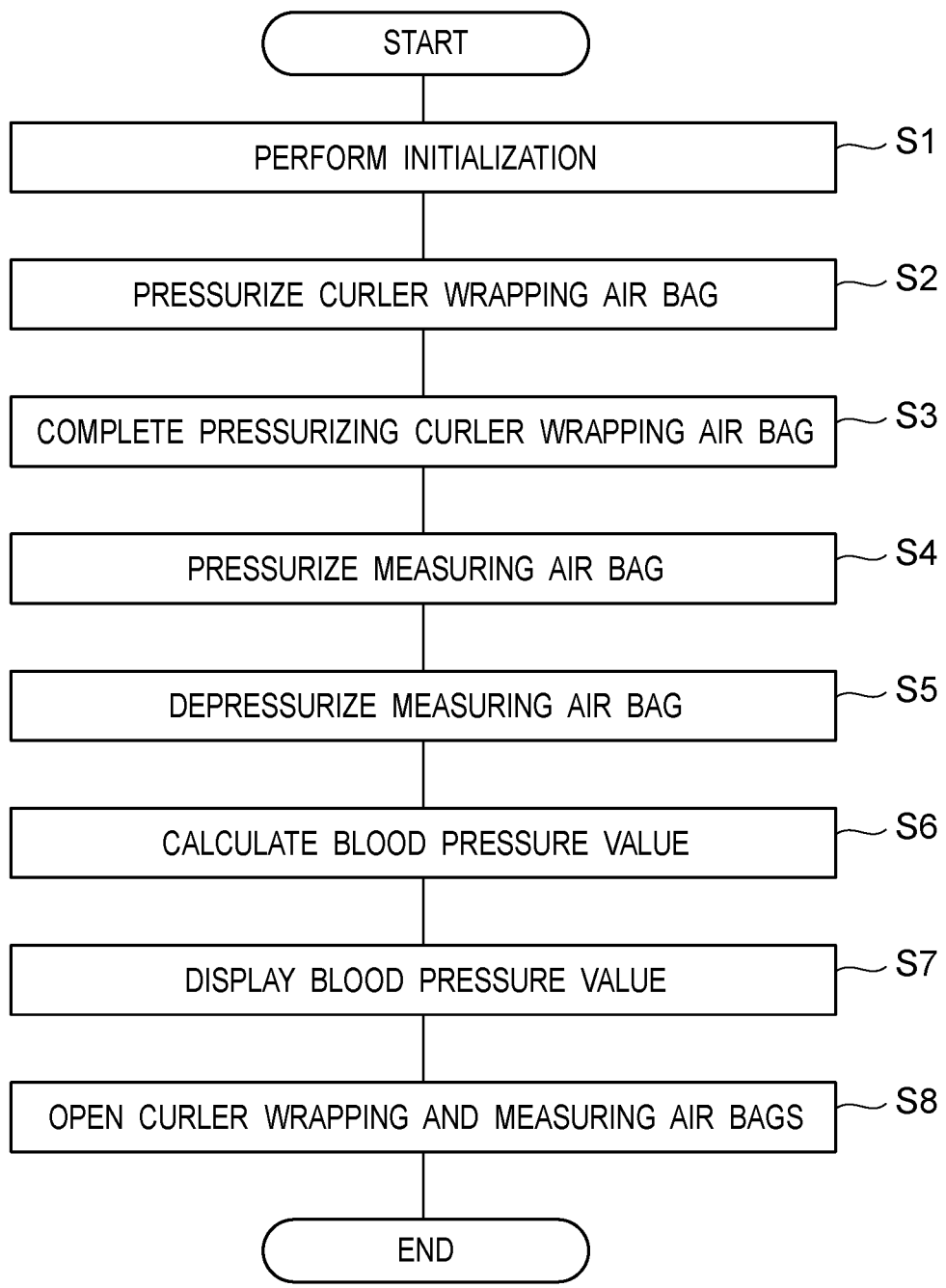

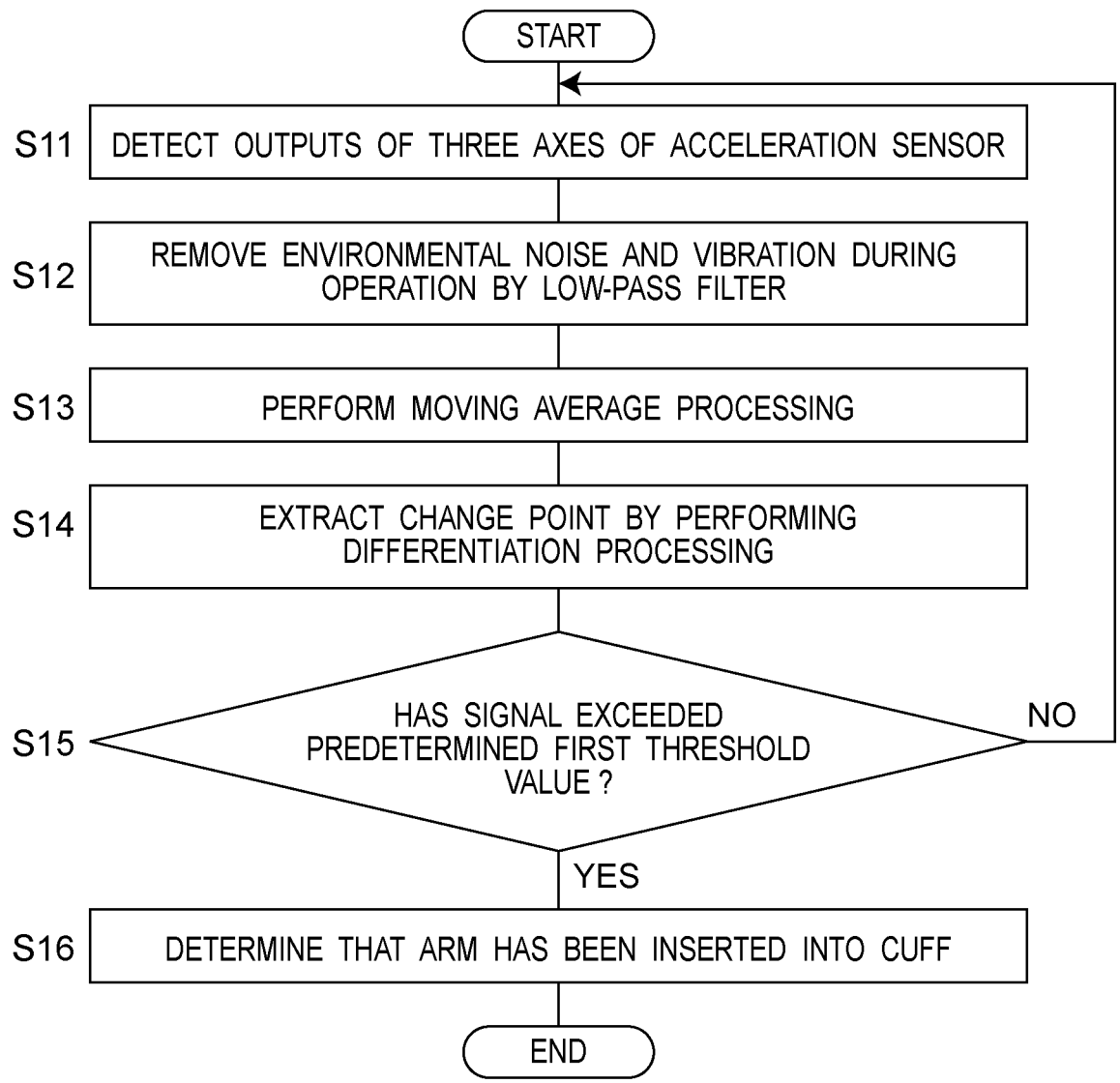

STANDBY STATE

LOWER LIMIT POSITION

BLOOD PRESSURE METER

CROSS-REFERENCE TO RELATED APPLICATION

This is a continuation application of International Application No. PCT/JP2019/007721, with an International filing date of Feb. 28, 2019, which claims priority of Japanese Patent Application No. 2018-081749 filed on Apr. 20, 2018, the entire content of which is hereby incorporated by reference.

TECHNICAL FIELD

The present invention relates to a sphygmomanometer, and more particularly, to a sphygmomanometer including a main body and a tubular cuff rotatably attached to a rotating shaft that is horizontal to the main body.

BACKGROUND ART

Conventionally, as this type of sphygmomanometer, for example, there is known one disclosed in Patent Literature 1 (JP 2010-136924 A) including a main body accommodating a pump and a cylindrical cuff (upper arm insertion part) rotatably attached to a rotating shaft that is horizontal to the main body. An air bag is provided along the inner circumferential surface of the cuff. A subject who is to perform blood pressure measurement inserts one's upper arm into the cuff while adjusting a tilt angle of the cuff. During blood pressure measurement, in a state of the subject inserting the upper arm into the cuff and taking a correct measurement posture (posture suitable for blood pressure measurement), air is supplied from the pump of the main body to the air bag of the cuff to compress the upper arm. Thereby, the blood pressure measurement is performed.

SUMMARY OF INVENTION

However, in the above-described sphygmomanometer, the subject must adjust the tilt angle of the cuff by oneself. In other words, the subject needs to find an appropriate angle by inserting one's upper arm into the cuff, temporarily stopping the cuff at a tilt angle that seems to be generally appropriate, and confirming that he/she is in a comfortable posture. If the subject is not in the comfortable posture, he/she needs to change the tilt angle slightly and confirms again to be in the comfortable posture. As a result, it takes a long time for the subject to take a correct measurement posture after inserting the upper arm into the cuff. Further, the blood pressure may be measured in an uncomfortable posture while the tilt angle of the cuff is inappropriate.

Accordingly, it is an object of the present invention to provide a sphygmomanometer including a main body and a tubular cuff rotatably attached to a rotating shaft that is horizontal to the main body, and allowing subjects having various body sizes to easily insert the upper arms into the cuff and to take the correct measurement posture in a short time.

In order to solve the above-mentioned problem, a sphygmomanometer of the present disclosure comprises:
a main body; and
a cuff having a cylindrical shape, rotatably attached to the main body about a rotating shaft horizontal to the main body, and into which an upper arm of a subject is inserted,
wherein the cuff has a fluid bag configured to compress the upper arm of the subject along an inner circumferential surface of the cuff, and is attached to the rotating shaft on a rear surface side opposite to a front surface side arranged facing the subject during blood pressure measurement, in a direction in which a central axis of the cuff extends, and
wherein the sphygmomanometer further comprises a swing mechanism configured to maintain, in a standby state of the upper arm not being inserted into the cuff, a tilt angle of the central axis of the cuff with respect to a horizontal plane at a standby angle at which the front surface side is higher than the rear surface side, and by the upper arm being inserted into the cuff, allow the tilt angle of the central axis of the cuff with respect to the horizontal plane to become either larger or smaller than the standby angle, and
wherein the swing mechanism includes:
a first coil spring erected at a position in the main body facing a first portion on the front surface side of the cuff; and
a second coil spring erected at a position in the main body facing a second portion between the first portion and the rotating shaft in a front-back direction,
wherein the first coil spring has a length in a natural state longer than a length of the second coil spring in the natural state, and the first coil spring has a spring constant set smaller than a spring constant of the second coil spring, and
wherein, in the standby state, by the first portion of the cuff compressing the first coil spring from the natural length by a weight of the cuff and the second portion of the cuff abutting on an upper end of the second coil spring, the tilt angle of the central axis of the cuff with respect to the horizontal plane is maintained at the standby angle.

As used herein, the "main body" may be, for example, a main body accommodating a pump or a part thereof (e.g., a main body lower part).

Further, the phrase the cuff is "attached" to the main body includes not only the case of the cuff being attached non-detachably but also the case of the cuff being attached detachably.

The "tubular" of the "tubular cuff" is typically cylindrical, but the cross section of the outer circumferential surface of the cuff may be polygonal or any other shape.

Further, the "standby angle" is typically set in accordance with a subject having a standard body size. Generally, for a subject having a large body size, the appropriate tilt angle of the cuff with respect to the horizontal plane (main body) is large, and for a subject having a small body size, the appropriate tilt angle of the cuff with respect to the horizontal plane (main body) is small (see, for example, Japanese Patent No. 5287572).

In another aspect, a sphygmomanometer of the present disclosure comprises:
a main body; and
a cuff having a cylindrical shape, rotatably attached to the main body about a rotating shaft horizontal to the main body, and into which an upper arm of a subject is inserted,
wherein the cuff has a fluid bag configured to compress the upper arm of the subject along an inner circumferential surface of the cuff, and is attached to the rotating shaft on a rear surface side opposite to a front surface side arranged facing the subject during blood pressure measurement, in a direction in which a central axis of the cuff extends, and wherein the sphygmomanometer further comprises a swing mechanism configured to maintain, in a standby state of the upper arm not being inserted into the cuff, a tilt angle of the central axis of the cuff with respect to a horizontal plane at a standby angle at which the front surface side is higher than the rear surface side, and by the upper arm being inserted into the cuff, allow the tilt angle of the central axis of the cuff with respect to the horizontal plane to become either larger or smaller than the standby angle, and wherein the sphygmomanometer further comprises:
an acceleration sensor integrally attached to the cuff, and
an arm insertion determination unit that determines, based on a change in an output of the acceleration sensor, whether or not an arm has been inserted into the cuff.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 16 is a diagram showing an operation flow of blood pressure measurement in the sphygmomanometer.

FIG. 17 is a diagram showing a flow for detecting that an arm is inserted into the cuff in the sphygmomanometer.

DESCRIPTION OF EMBODIMENTS

Hereinafter, an embodiment of the present invention is described in detail with reference to the drawings.

(Schematic Configuration of Main Body)

Figure 1:
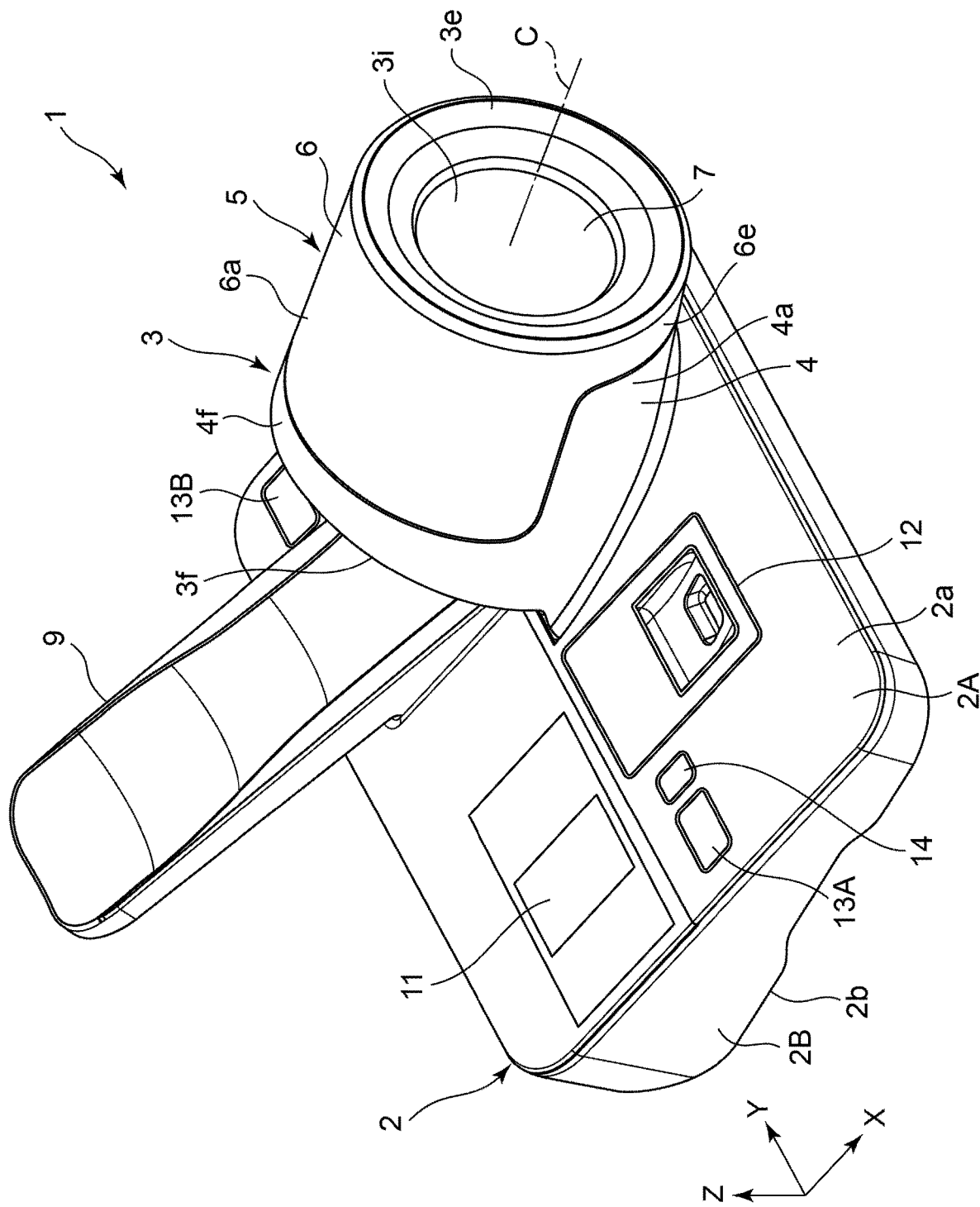
FIG. 1 is a diagram showing a sphygmomanometer having a main body and a cuff as viewed diagonally from above and front, according to one embodiment of the present invention.
Figure 2:
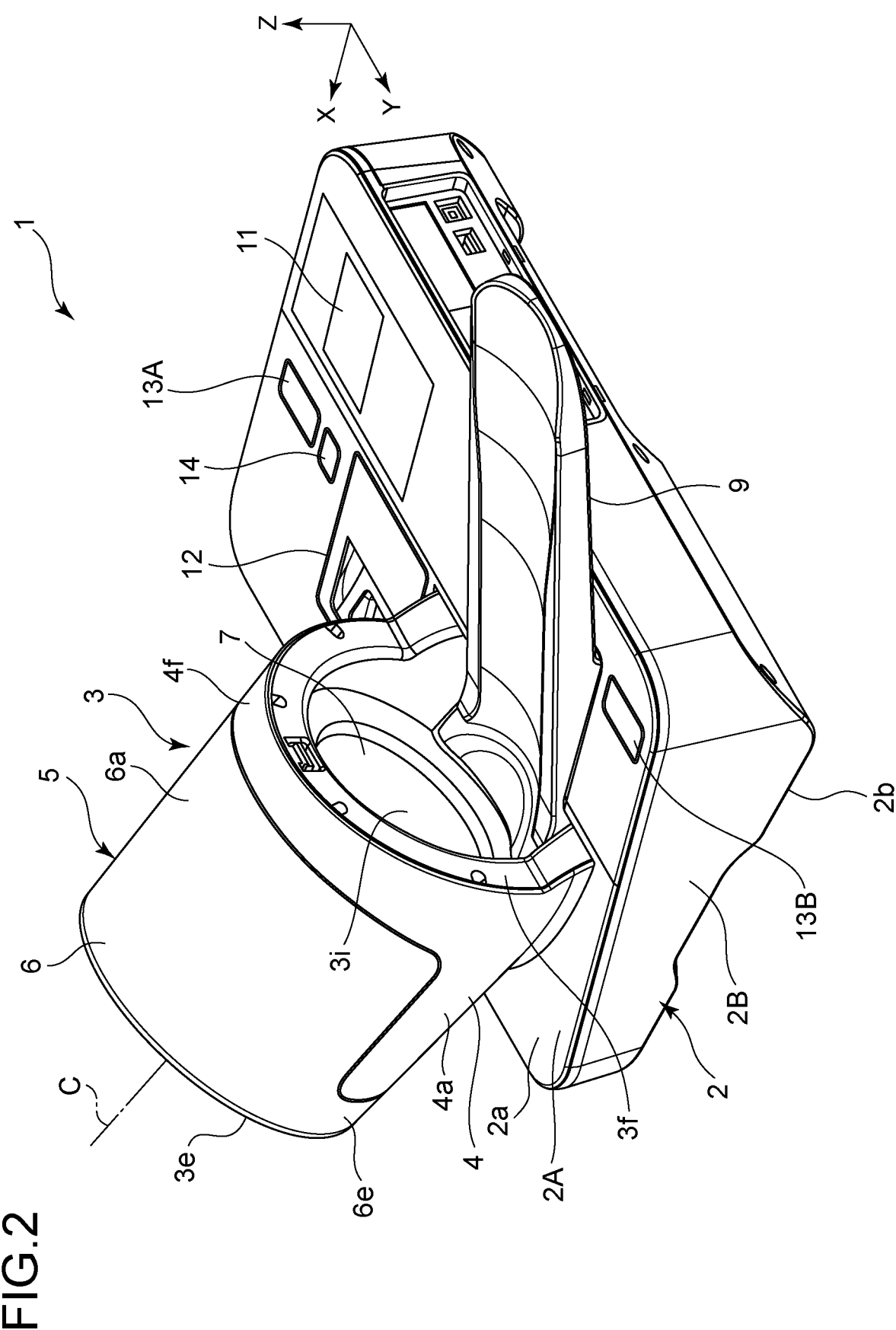
FIG. 2 is a diagram showing the sphygmomanometer as viewed diagonally from above and rear.
Figure 3:
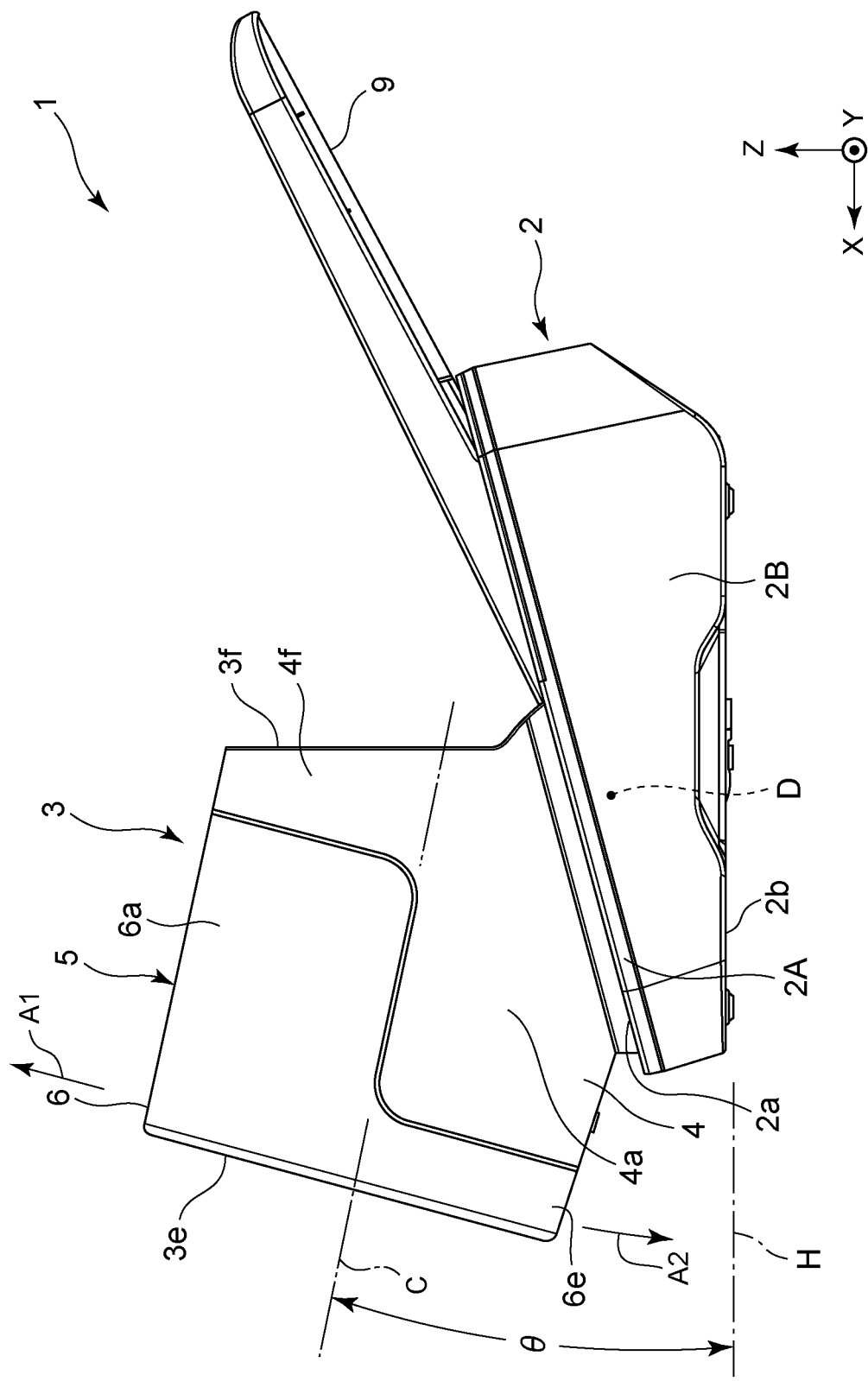
FIG. 3 is a diagram showing the sphygmomanometer as viewed from the right side.

FIG. 1 shows a sphygmomanometer (indicated by reference numeral 1) of one embodiment of the present invention as viewed from diagonally above and front. FIG. 2 shows the sphygmomanometer 1 as viewed diagonally from above and rear. Further, FIG. 3 shows the sphygmomanometer 1 as viewed from the right side. Note that these FIGS. 1 to 3 (and FIGS. 4, 6, 7, 9 to 13, 19A to 19C described later) also show an XYZ orthogonal coordinate system for easy understanding. The X-axis is oriented in the front-back direction, the Y-axis is oriented in the left-right direction, and the Z-axis is oriented in the up-down direction. As shown in FIGS. 1 to 3, the sphygmomanometer 1 generally includes a main body 2, a cuff 3, and an armrest 9. The sphygmomanometer 1 is designed to measure the blood pressure of the upper arm of a subject as a measurement target site.

The main body 2 has a box-like outer shape with rounded corners, and includes a main body upper part 2A and a main body lower part 2B. A bottom surface 2b of the main body lower part 2B is substantially flat and is placed on a table 99 (see FIGS. 9 to 11) along a horizontal plane (parallel to the XY plane). An upper surface 2a of the main body upper part 2A is substantially flat and is tilted in a manner of gradually increasing in height (increasing in Z coordinate) from the front to the rear (in the −X direction).

The cuff 3 having a substantially cylindrical shape is arranged on the right front part of the upper surface 2a of the main body upper part 2A. In this example, a central axis of the cuff 3 (that is, a central axis of a cuff housing 4 described later) C is tilted in a manner of gradually decreasing in height (decreasing in Z coordinate) from the front to the rear (in the −X direction).

The armrest 9 is arranged on the right rear part of the upper surface 2a of the main body upper part 2A. The armrest 9 has a substantially circular-arc cross section that opens upward, and extends substantially straight and rearward of the main body 2 from an opening on the rear surface side of the cuff 3 at a steeper tilt than the tilt of the upper surface 2a of the main body upper part 2A. During blood pressure measurement, the subject sits in front of the main body 2 and passes the arm from the front surface 3e side (side facing the subject) to the rear surface 3f side of the cuff 3 such that an upper arm 90 of the subject (see FIGS. 9 to 11) is expected to be placed inside the cuff 3 and the forearm is expected to be placed on the armrest 9.

In the upper surface 2a of the main body upper part 2A, there are provided on the left front part, a measurement start/stop switch 13A for allowing a user (mainly a subject. The same applies hereinafter), to instruct the start or stop of measurement with the left hand, and a print instruction switch 14 for allowing the user to instruct printing of the blood pressure measurement result. In the upper surface 2a of the main body upper part 2A, there is arranged on the left rear part, a display (a liquid crystal display (LCD) in this example) 11 for displaying the blood pressure measurement result. The display 11 may be erected on the upper surface 2a of the main body upper part 2A such that a display screen faces the subject. Further, in the upper surface 2a of the main body upper part 2A, there is arranged on the further right side of the armrest 9, a measurement start/stop switch 13B for allowing the user to instruct the start or stop of the measurement with the right hand. The two measurement start/stop switches 13A and 13B are provided for convenience when the subject passes the right upper arm or left upper arm through the cuff 3 for measurement.

In this example, the cuff 3 is constituted of the cuff housing 4 provided in the main body 2 and a cylindrical cuff unit 5 detachably attached to the cuff housing 4.

Figure 4:
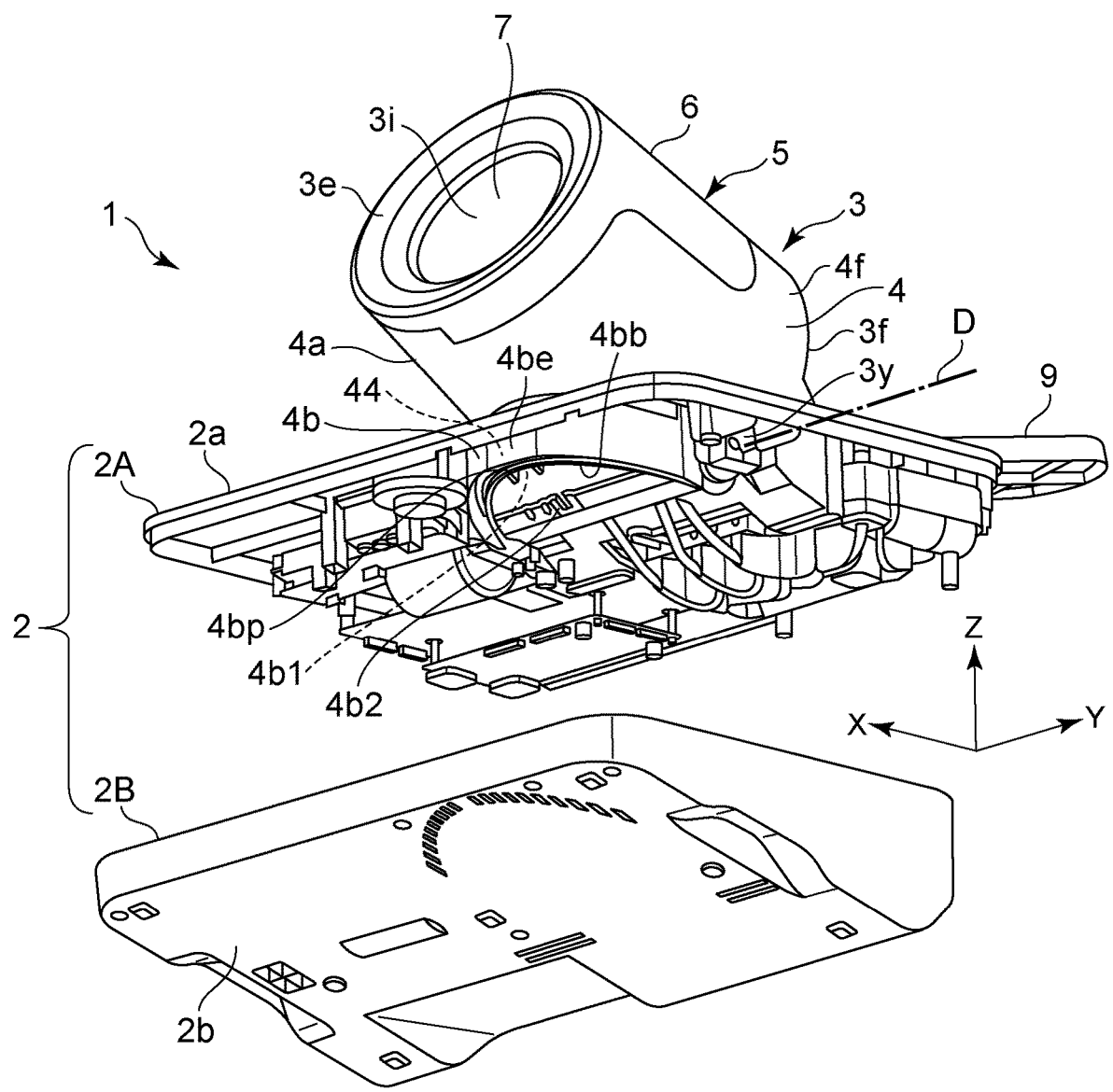
FIG. 4 is a diagram showing the sphygmomanometer as viewed diagonally from below and front, with upper and lower parts of the main body disassembled.

The cuff housing 4 integrally includes a front surface side portion 4a having a circular-arc (in this example, semi-circular) cross section that opens upward, a rear surface side portion 4f connected to the rear of the front surface side portion 4a and having a circular cross-section concentric (about central axis C) with the circular-arc cross section of the front surface side portion 4a, and a cuff housing lower part 4b (shown in FIG. 4) accommodated in the main body 2. In this example, the cuff housing 4 is made of acrylonitrile-butadiene-styrene (ABS) resin. As shown in FIG. 4 (in which the main body upper part 2A and the main body lower part 2B are disassembled), the cuff housing lower part 4b has a substantially semi-cylindrical shape that opens rearward. A pair of hinges 3y (only the right hinge is shown in FIG. 4) are provided on the left and right sides of the rear surface 3f side of the cuff housing lower part 4b. With this pair of hinges 3y, as shown in FIG. 3, the cuff 3 is attached rotatably as shown by arrows A1 and A2 about a rotating shaft D that is horizontal to the main body 2.

As shown in FIG. 4, the cuff housing lower part 4b is provided with, at a lower edge 4bb, a protrusion 4bp protruding forward at a portion corresponding to substantially the center in the left-right direction (Y direction). Further, at a portion closer to the front surface side (+X direction) in the cuff housing lower part 4b, an acceleration sensor 44 mounted on a not-shown circuit board is provided integrally with the cuff housing lower part 4b (i.e., with the cuff 3). The functions of these elements are described later.

(Cuff Unit)

Figure 6:
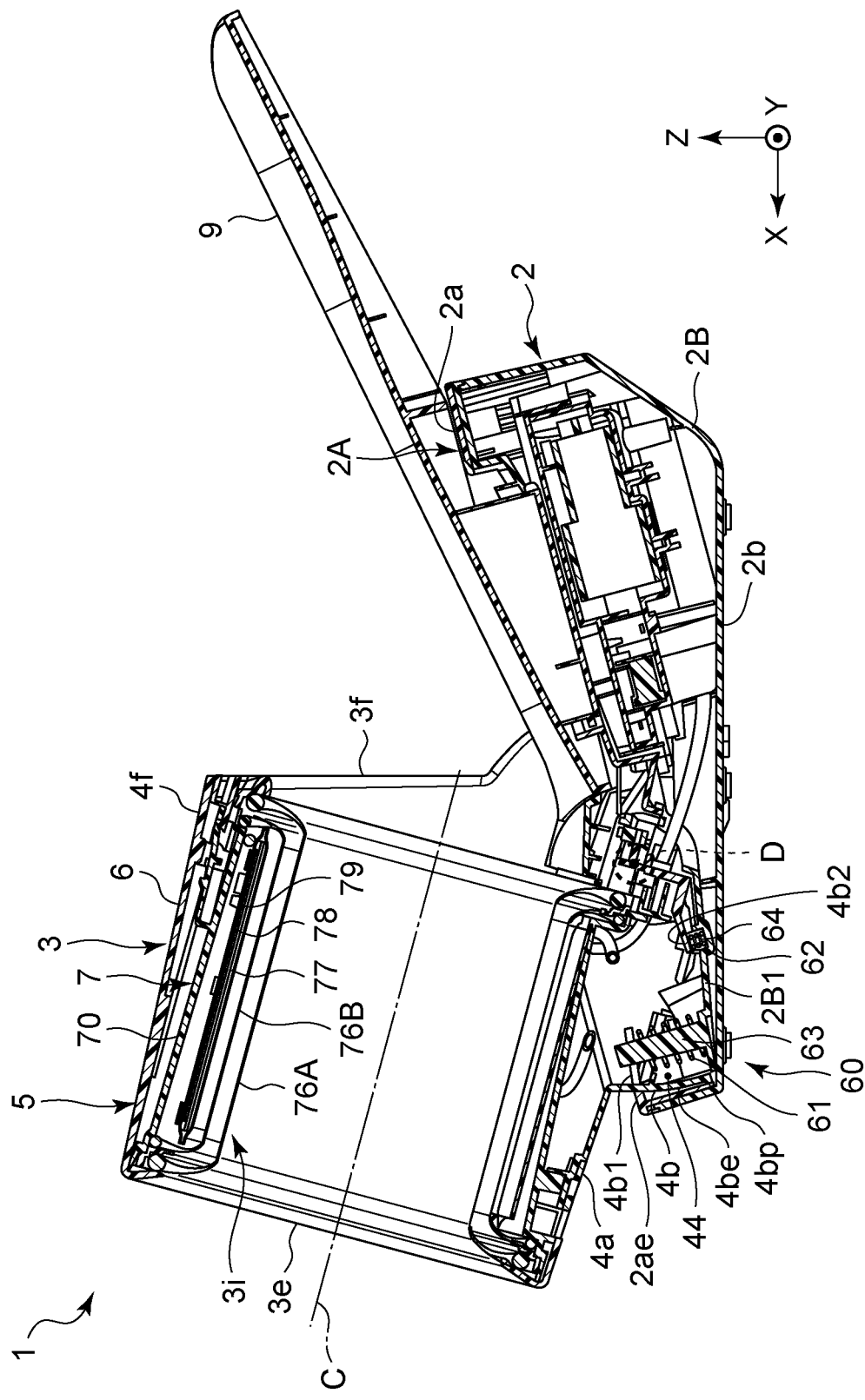
FIG. 6 is a diagram showing a cross section of the sphygmomanometer as viewed from the right side.

As shown in FIG. 6 (showing a cross section when the sphygmomanometer 1 is viewed from the right side), the cuff unit 5 is constituted of a cuff structure 7 having a cylindrical shape into which the upper arm 90 is inserted, and a cover 6 detachably attached integrally with the cuff structure 7.

The cuff structure 7 includes a base member 70 formed of plastic material (for example, polyvinyl chloride) having a cylindrical shape. A curler wrapping air bag 79, a curler 78, a measuring air bag 77, an inner cover 76B, and an outer cover 76A are provided sequentially along the inner circumferential surface of the base member 70. In this example, the outer cover 76A corresponds to the inner circumferential surface 3i of the cuff 3, and the curler wrapping air bag 79 and the measuring air bag 77 correspond to fluid bags.

The outer cover 76A is made of a cylindrical stretchable cloth having not-shown folds. The inner cover 76B is made of cushion material (for example, foam sponge material) having a cylindrical shape and a larger thickness than the outer cover 76A to prevent the upper arm 90 from being hurt during measurement. The outer cover 76A and the inner cover 76B are detachable from the base member 70. For example, when being stained, the outer cover 76A may be removed, washed, and then attached again.

Figure 14A:
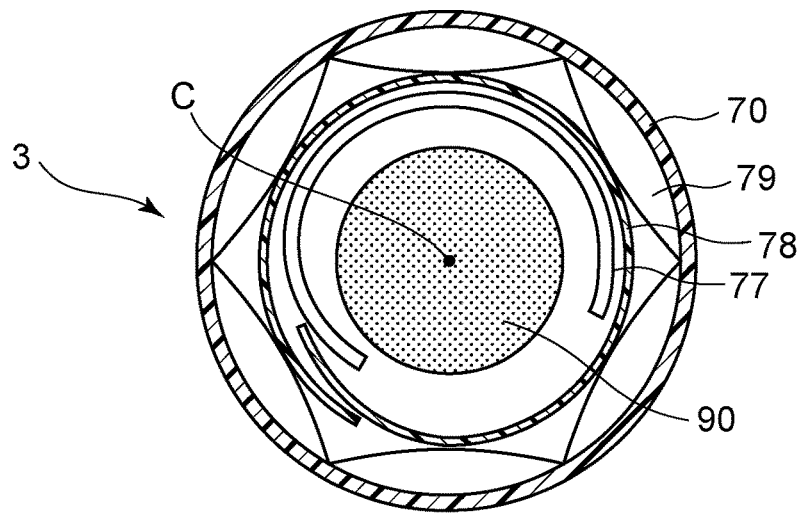
FIG. 14A to FIG. 14C are diagrams showing an operation of a cuff structure included in the cuff during blood pressure measurement.
Figure 14B:
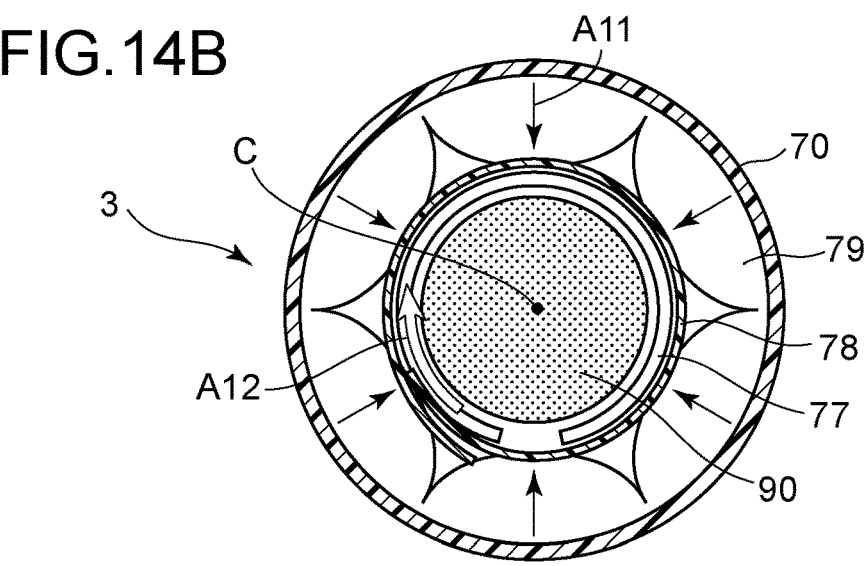

The curler wrapping air bag 79 is made of a stretchable resin (for example, polyurethane). As shown in FIG. 14A (showing a cross section perpendicular to the central axis C of the cuff 3), in this example, the curler wrapping air bag 79 is provided along the inner circumferential surface of the base member 70 while being divided in six sections.

The curler 78 is made of a resin having an appropriate flexibility (for example, polypropylene), and is produced to have a flat plate shape in the developed state, but have a substantially annular shape surrounding the upper arm 90 in the state of FIG. 14A (natural state), and such that the end portions in the circumferential direction overlap with each other.

The measuring air bag 77 is made of a stretchable resin (for example, polyurethane), similarly to the curler wrapping air bag 79. This measuring air bag 77 is set to a length (circumferential dimension) such that substantially two-thirds or more of the upper arm 90 along the inner circumferential surface of the curler 78 can be wrapped. (However, in the state of FIG. 14A, the circumferential ends of the measuring air bag 77 are relatively far apart from each other.)

As can be seen from FIGS. 1 to 3, the cover 6 integrally includes a rear surface side portion 6a having a circular-arc (in this example, a semi-circular) cross section that opens downward, and a front surface side portion (portion on the side facing the subject) 6e connected to the front of the rear surface side portion 6a and having a circular cross-section concentric (about central axis C) with the circular-arc cross section of the rear surface side portion 6a. Similarly to the cuff housing 4, the cover 6 is made of ABS resin in this example. With the sphygmomanometer 1 set up, no gap is created between the cover 6 and the cuff housing 4.

(Swing Mechanism)

As shown in FIG. 6, the sphygmomanometer 1 includes a swing mechanism 60 that allows the cuff 3 to swing about the rotating shaft D with respect to the main body 2. The swing mechanism 60 includes a first coil spring 61 and a second coil spring 62. In this example, the swing mechanism 60 is substantially simply configured by adding two members which are the first coil spring 61 and the second coil spring 62.

Figure 7:
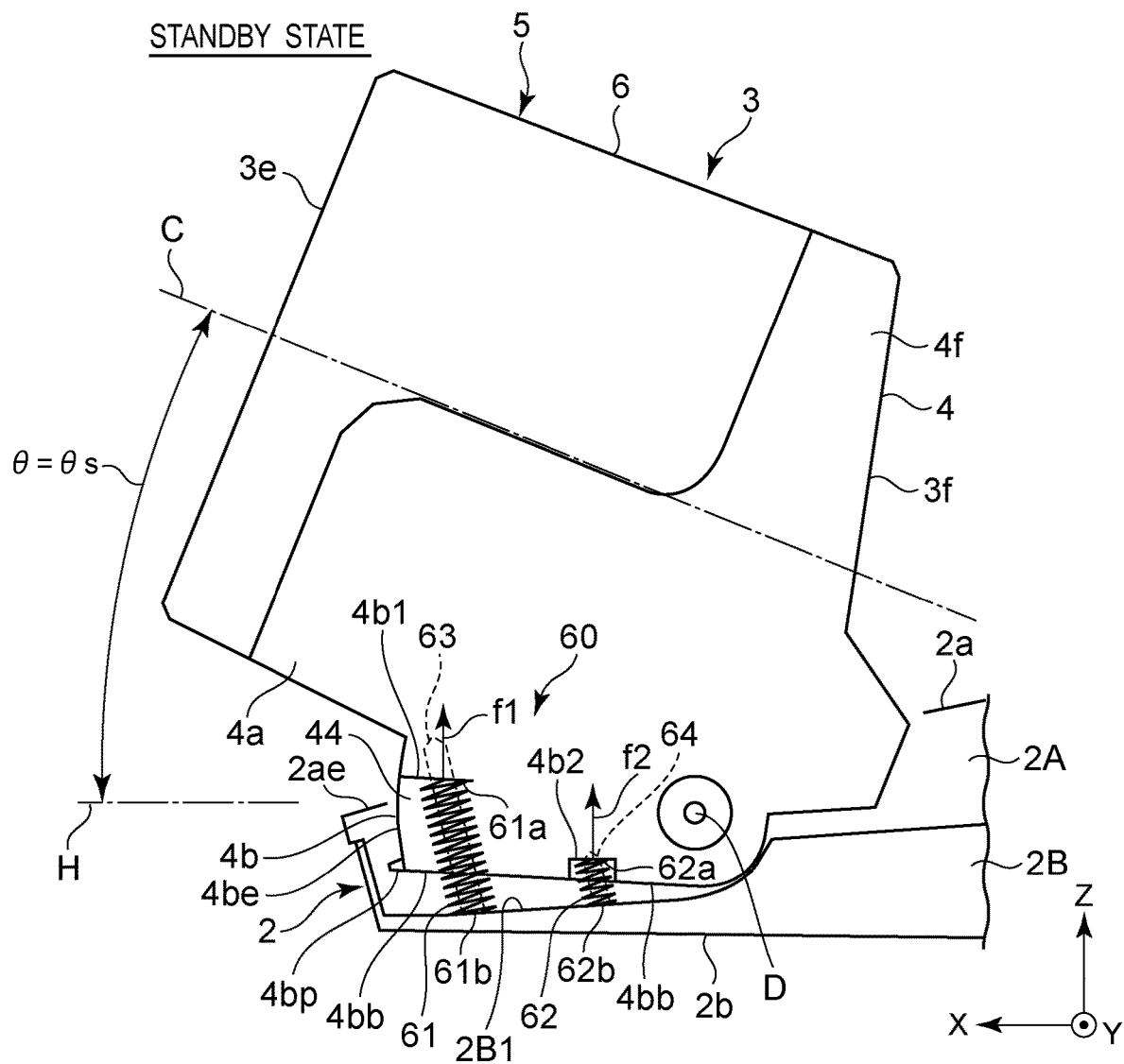
FIG. 7 is a diagram schematically showing a configuration of a swing mechanism that allows the cuff to swing with respect to the main body in the sphygmomanometer.

As schematically shown in FIG. 7, the first coil spring 61 is erected at a position in the main body lower part 2B facing a first portion 4b1 on the front surface 3e side of the cuff 3. The second coil spring 62 is erected at a position in the main body lower part 2B facing a second portion 4b2 between the first portion 4b1 and the rotating shaft D in the front-back direction (X direction). As shown in FIG. 4, the first portion 4b1 and the second portion 4b2 of the cuff 3 are both located substantially in the center of the cuff housing lower part 4b in the left-right direction (Y direction). Therefore, the first coil spring 61 and the second coil spring 62 are both located below the cuff 3 and substantially in the center of the cuff 3 in the left-right direction (Y direction).

As can be seen from FIG. 7, the main body lower part 2B is provided with a tilted plate part 2B1 that is gently tilted (more gently than the upper surface 2a) immediately above the horizontal bottom surface 2b in a manner of gradually increasing in height (increasing in Z coordinate) from the front to the rear (in the −X direction). A first mandrel 63 and a second mandrel 64 that extend straight upward are erected substantially vertically to the tilted plate part 211. In this example, the first mandrel 63 and the second mandrel 64 are integrally formed with the tilted plate part 2B1 by integral molding so as not to increase the number of members of the swing mechanism 60. The first coil spring 61 and the second coil spring 62 are in a state of being fitted around the first mandrel 63 and the second mandrel 64, respectively. In this state, a lower end 61b of the first coil spring 61 and a lower end 62b of the second coil spring 62 are attached and fixed to the tilted plate part 2B1. Therefore, even if the compression and expansion of the first coil spring 61 and the second coil spring 62 are repeated as the sphygmomanometer 1 is used, the first coil spring 61 and the second coil spring 62 are firmly and stably held at the positions in the main body lower part 2B where the first coil spring 61 and the second coil spring 62 are erected. On the other hand, neither an upper end 61a of the first coil spring 61 nor an upper end 62a of the second coil spring 62 is attached to the first portion 4b1 and the second portion 4b2 of the cuff 3 and is free. (However, in FIG. 7, the upper end 61a of the first coil spring 61 and the upper end 62a of the second coil spring 62 are in contact with the first portion 4b1 and the second portion 4b2 of the cuff 3, respectively.)

Figure 8:
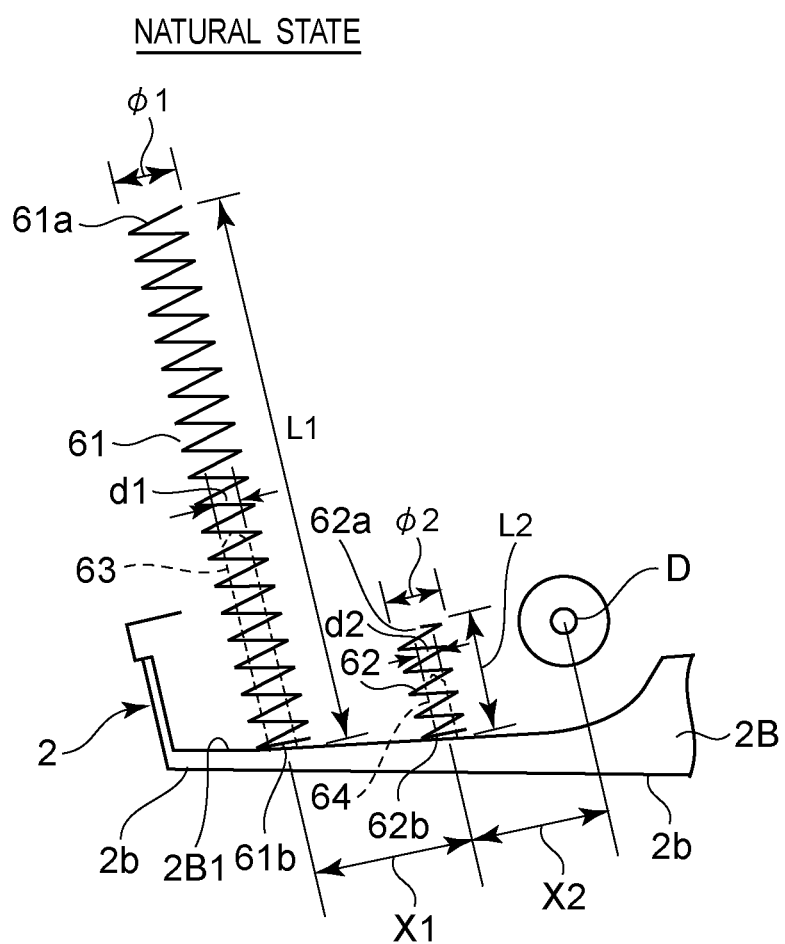
FIG. 8 is a diagram showing an aspect of the first coil spring and the second coil spring in a natural state.

As shown in FIG. 8, a length L1 of the first coil spring 61 in the natural state is longer than a length L2 of the second coil spring 62 in the natural state, and a spring constant k1 of the first coil spring 61 is set smaller than a spring constant k2 of the second coil spring 62. Further, in this example, a diameter φ1 of the first coil spring 61 is set larger than a diameter φ2 of the second coil spring 62. Accordingly, a diameter d1 of the first mandrel 63 is set larger than a diameter d2 of the second mandrel 64.

Specifically, the specifications of the first coil spring 61 and the second coil spring 62 are set as shown in Table 1 below. A distance X1 between the first coil spring 61 and the second coil spring 62 along the tilted plate part 2B1 is set to X1=42 mm, and a distance X2 between the second coil spring 62 and the rotating shaft D is set to X2=39 mm.

TABLE 1

Specifications of coil springs

| | Diameter [mm] | Length in natural state [mm] | Spring constant [N/mm] |
|---|---|---|---|
| First coil spring | φ1 = 20 | L1 = 50 | k1 = 0.3 |

TABLE 1-continued

Specifications of coil springs

| | Diameter [mm] | Length in natural state [mm] | Spring constant [N/mm] |
|---|---|---|---|
| Second coil spring | φ2 = 10 | L2 = 10 | k2 = 2.0 |

Figure 5:
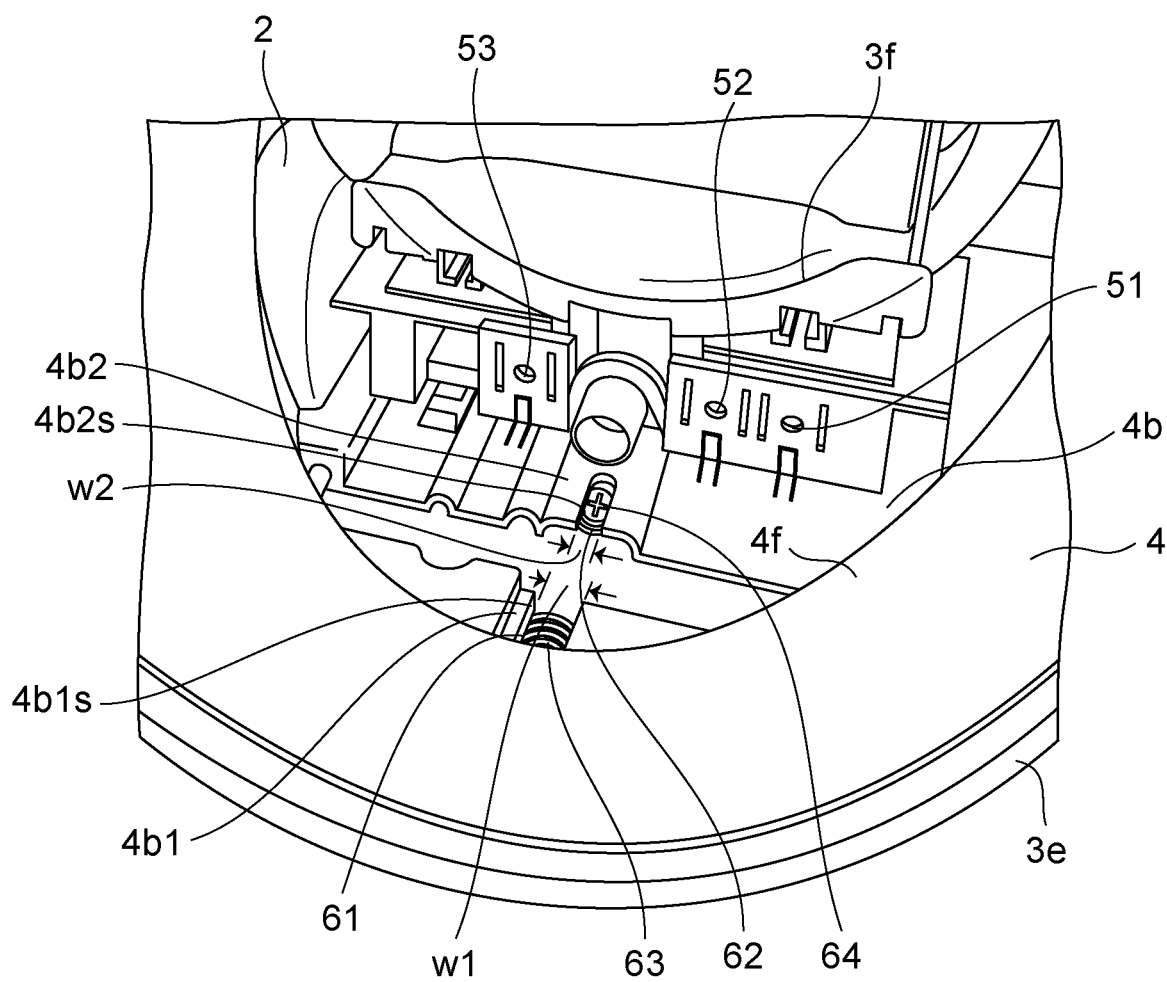
FIG. 5 is a diagram showing aspects of a first coil spring and a second coil spring provided in the main body, and a first portion and a second portions of the cuff facing the upper ends of the first coil spring and the second coil spring, respectively, as viewed from above and front, with a cuff unit removed from the main body.

FIG. 5 shows an aspect of the first coil spring 61 and the second coil spring 62 provided in the main body 2 and the first portion 4b1 and the second portion 4b2 of the cuff 3 that faces (or abut on) the upper ends of the first coil spring 61 and the second coil spring 62, respectively, as viewed from the front and above in a state of the cuff unit 5 being removed from the main body 2. As shown in FIG. 5, the first portion 4b1 and the second portion 4b2 of the cuff 3 are provided with a first slit 4b1s as a first relief part and a second slit 4b2s as a second relief part that allow the first mandrel 63 and the second mandrel 64 to pass through, respectively, as the cuff 3 rotates about the rotating shaft D. In this example, a width (dimension in the Y direction) w1 of the first slit 4b1s is set to a value between the diameter d1 of the first mandrel 63 and the diameter φ1 of the first coil spring 61. Similarly, a width (dimension in the Y direction) w2 of the second slit 4b2s is set to a value between the diameter d2 of the second mandrel 64 and the diameter φ2 of the second coil spring 62. As a result, as the cuff 3 rotates downward about the rotating shaft D, the first portion 4b1 and the second portion 4b2 of the cuff 3 allow the first mandrel 63 and the second mandrel 64 to pass through without interfering with the first mandrel 63 and the second mandrel 64. On the other hand, the first portion 4b1 and the second portion 4b2 of the cuff 3 do not allow the upper end 61a of the first coil spring 61 and the upper end 62a of the second coil spring 62 to pass through. Therefore, as the cuff 3 rotates downward about the rotating shaft D, the first coil spring 61 and the second coil spring 62 are compressed by the first portion 4b1 and the second portion 4b2 of the cuff 3, respectively. Conversely, as the cuff 3 rotates upward about the rotating shaft D, each of the first coil spring 61 and the second coil spring 62 expands.

As shown in FIG. 7, in the standby state of the upper arm 90 not being inserted into the cuff 3, the weight of the cuff 3 (about 1 kg in this example) causes the first portion 4b1 of the cuff 3 to compress the first coil spring 61 from the length L1 in the natural length, and causes the second portion 4b2 of the cuff 3 to abut on the upper end 62a of the second coil spring 62. More specifically, in the standby state, the weight of the cuff 3 causes the cuff 3 to rotate about the rotating shaft D, and thus the first portion 4b1 of the cuff 3 compresses the first coil spring 61 from the length L1 in the natural state. Here, because the spring constant k1 of the first coil spring 61 is set relatively small (smaller than the spring constant k2 of the second coil spring 62), the first coil spring 61 is easily compressed from the length L1 in the natural state to become short in length. As a result, the second portion 4b2 of the cuff 3 abuts on the upper end 62a of the second coil spring 62. Note that, because the spring constant k2 of the second coil spring 62 is set relatively large (larger than the spring constant k1 of the first coil spring 61), the second coil spring 62 supports the weight of the cuff 3 by elastic force f1 of the first coil spring 61 and elastic force f2 of the second coil spring 62, by only becoming slightly shorter in length than the length L2 in the natural state. As a result, a tilt angle θ of the central axis C of the cuff 3 with respect to the horizontal plane H is maintained at a standby angle θs. In this example, in the standby state shown in FIG. 7, the elastic force of the first coil spring 61 is f1=10.41 N and the elastic force of the second coil spring 62 is f2=0.95 N.

The standby angle θs can be typically set in accordance with the subject having a standard body size. In this example, the standby angle θs=18° is set in accordance with a subject 81 (see FIG. 9) having the standard body size. In general, in the case of a subject 82 having a large body size (see FIG. 10), the appropriate tilt angle θ of the cuff 3 with respect to the horizontal plane H becomes large, and in the case of a subject 83 having a small body size (see FIG. 11), the appropriate tilt angle θ of the cuff 3 with respect to the horizontal plane H becomes small.

The swing mechanism 60 allows the tilt angle θ of the cuff 3 to become either larger or smaller than the standby angle s by the upper arm 90 being inserted into the cuff 3. Therefore, according to the sphygmomanometer 1, the subjects 81 to 83 having various body sizes can easily insert the upper arms 90 into the cuff 3.

Figure 9:
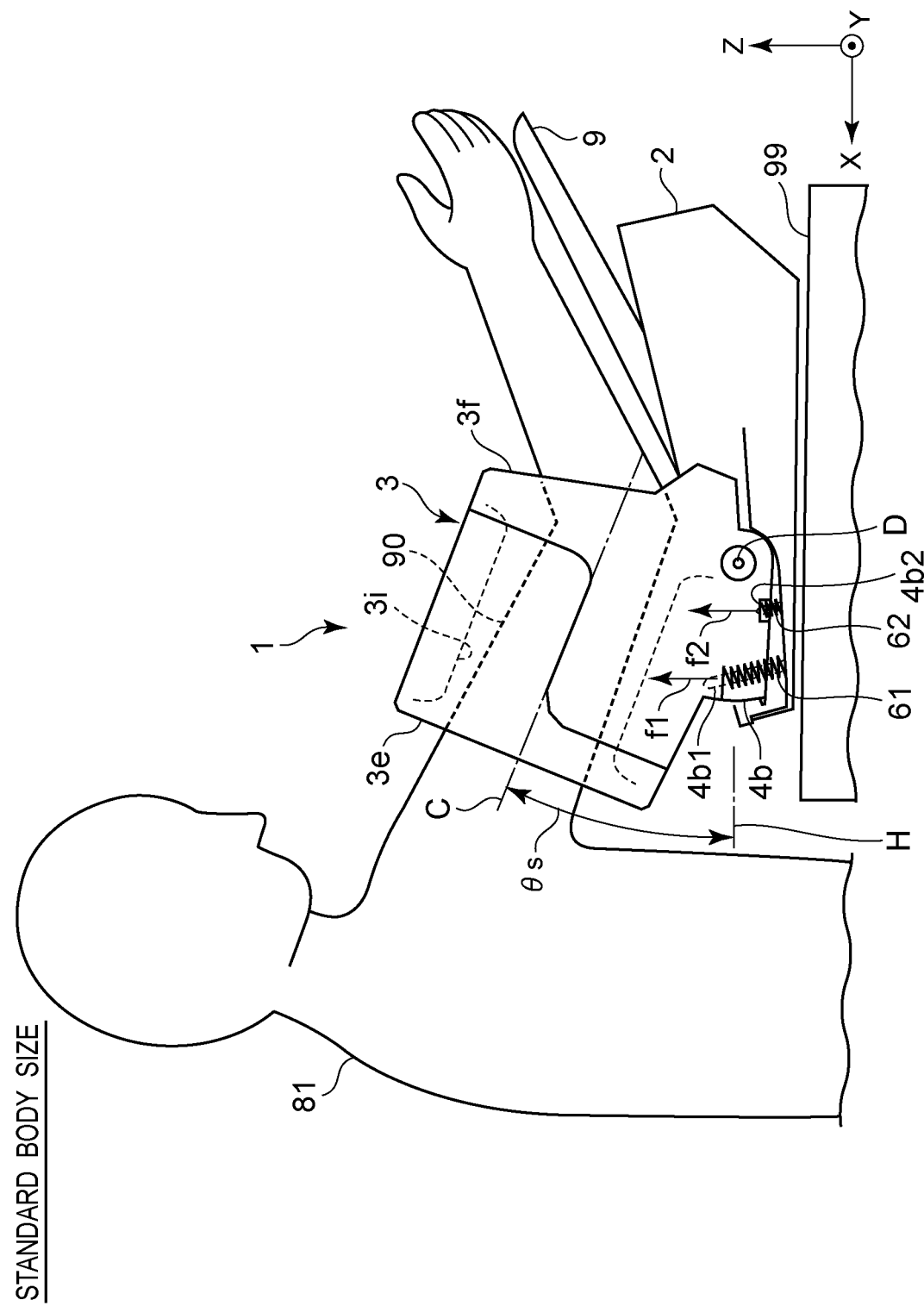
FIG. 9 is a diagram schematically showing a state in which a subject having a standard body size inserts one's upper arm into the cuff.

In addition, as shown in FIG. 9, in the case of the subject 81 having the standard body size, when the upper arm 90 is inserted into the cuff 3, an angle difference caused by rotating the tilt angle θ of the cuff 3 to an appropriate angle suitable for one's body size is appropriately zero. Therefore, the subject 81 does not need to find the tilt angle θ of the cuff 3. As a result, the subject 81 having the standard body size can take a correct measurement posture in a short time when inserting the upper arm 90 into the cuff 3.

Figure 10:
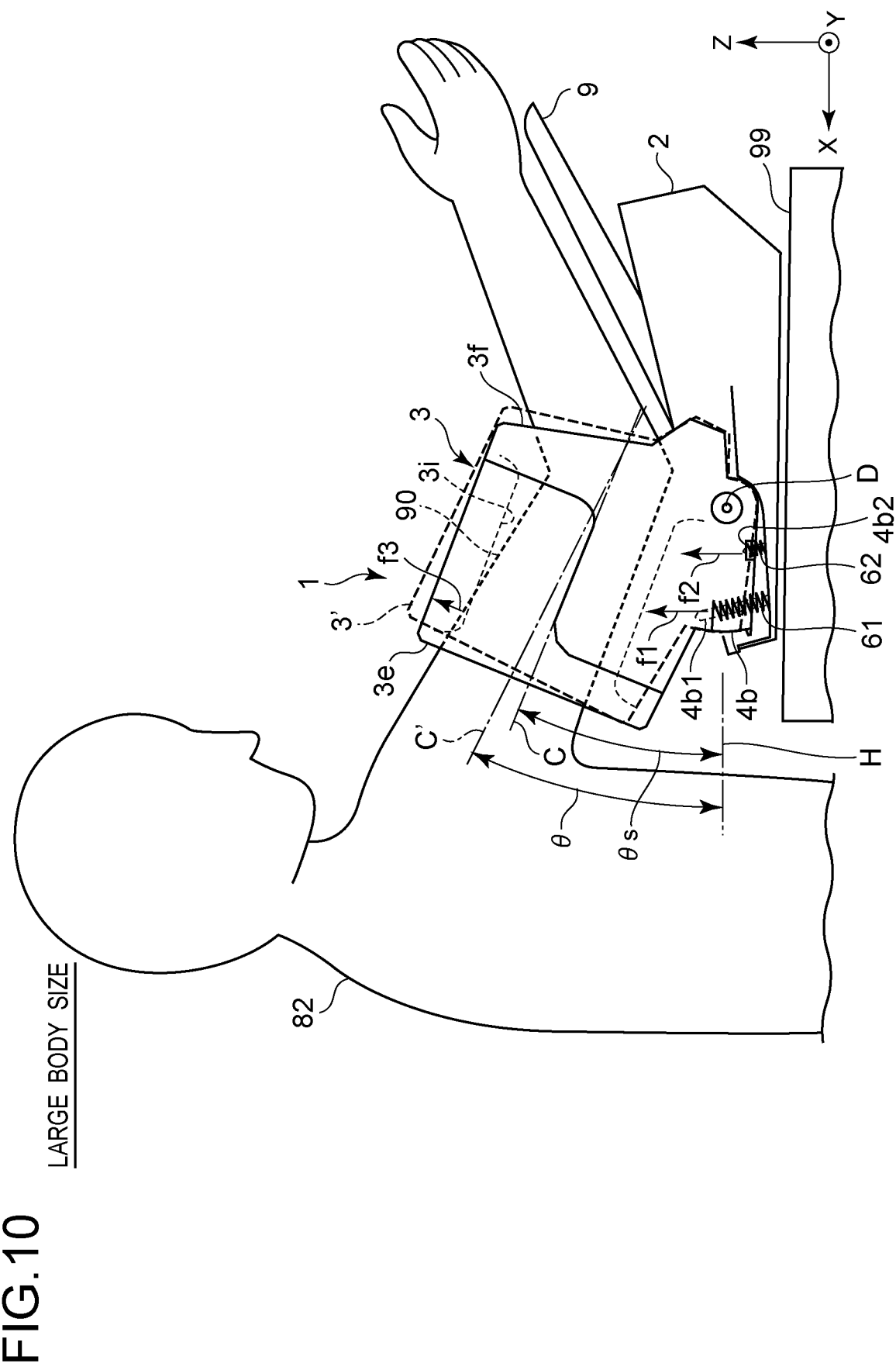
FIG. 10 is a diagram schematically showing a state in which a subject having a large body size inserts one's upper arm into the cuff.

In the case of the subject 82 having the large body size, the appropriate tilt angle θ of the cuff 3 with respect to the horizontal plane H becomes large as described above. In the above case, as shown in FIG. 10, because the upper arm 90 pushes the inner circumferential surface 3i of the cuff 3 upward by the upper arm 90 being inserted into the cuff 3 (in FIG. 10, this pushing force is indicated by an arrow f3), the tilt angle θ of the cuff 3 tends to become larger than the standby angle θs. Here, the swing mechanism 60 allows the tilt angle θ of the cuff 3 to become larger than the standby angle θs, as indicated by a one-dot chain line C' in FIG. 10. (A broken line 3' indicates a position of the cuff 3 according to a change in the tilt angle θ). Therefore, the tilt angle θ of the cuff 3 becomes large so as to follow the body size of the subject 82, and the subject 82 does not need to find the tilt angle θ of the cuff 3. As a result, the subject 82 having the large body size can take the correct measurement posture in a short time when inserting the upper arm 90 into the cuff 3.

More specifically, in the case of the subject 82 having the large body size, when the tilt angle θ of the cuff 3 tends to become larger than the standby angle θs by the upper arm 90 being inserted into the cuff 3, the first coil spring 61 expands as the height of the first portion 4b1 of the cuff 3 increases. Further, as the height of the second portion 4b2 of the cuff 3 increases, the second coil spring 62 also slightly expands, and when the height of the second portion 4b2 increases to some extent, the upper end 62a of the second coil spring 62 is separated from the second portion 4b2. In this way, the tilt angle θ of the cuff 3 is allowed to become larger than the standby angle θs. At this time, the first coil spring 61 pushes the first portion 4b1 of the cuff 3 upward by the elastic force f1 while expanding. (However, the elastic force f1 becomes smaller as the first coil spring 61 expands). Therefore, the force f3 with which the upper arm 90 of the subject 82 pushes the inner circumferential surface 3i of the cuff 3 upward only needs to be small. Therefore, the subject 82 having the large body size can easily take the correct measurement posture when inserting the upper arm 90 into the cuff 3.

Figure 11:
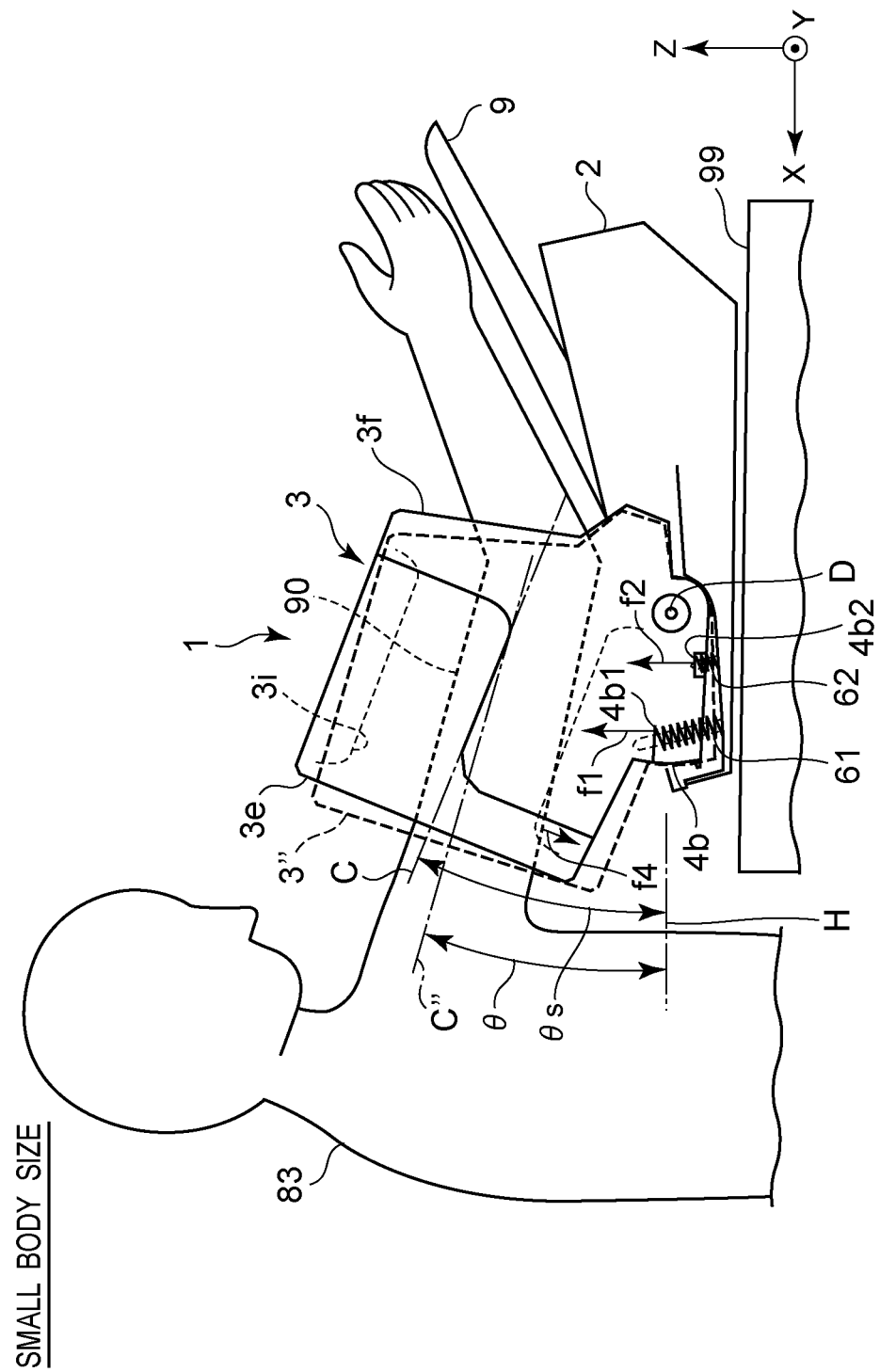
FIG. 11 is a diagram schematically showing a state in which a subject having a small body size inserts one's upper arm into the cuff.

On the other hand, in the case of the subject 83 having the small body size, the appropriate tilt angle θ of the cuff 3 with respect to the horizontal plane 11 becomes small as described above. In the above case, as shown in FIG. 11, because the upper arm 90 pushes the inner circumferential surface 3i of the cuff 3 downward by the upper arm 90 being inserted into the cuff 3 (in FIG. 11, this pushing force is indicated by an arrow f4), the tilt angle θ of the cuff 3 tends to become smaller than the standby angle θs. Here, the swing mechanism 60 allows the tilt angle θ of the cuff 3 to become smaller than the standby angle θs, as indicated by a one-dot chain line C" in FIG. 11. (A broken line 3" indicates a position of the cuff 3 according to a change in the tilt angle θ). Therefore, the tilt angle θ of the cuff 3 becomes smaller so as to follow the body size of the subject 83, and the subject 83 does not need to find the tilt angle θ of the cuff 3. As a result, the subject 83 having the small body size can take the correct measurement posture in a short time when inserting the upper arm 90 into the cuff 3.

More specifically, in the case of the subject 83 having the small body size, when the tilt angle θ of the cuff 3 tends to decrease from the standby angle θs by the upper arm 90 being inserted into the cuff 3, the first coil spring 61 contracts as the height of the first portion 4b1 of the cuff 3 decreases. Further, the second coil spring 62 also contracts as the height of the second portion 4b2 of the cuff 3 decreases. In this way, the tilt angle θ of the cuff 3 is allowed to become smaller than the standby angle θs. At this time, the force f4 with which the upper arm 90 of the subject 83 pushes the inner circumferential surface 3i of the cuff 3 downward is mainly due to the body weight, and therefore, the burden on the upper arm 90 of the subject 83 is small. Therefore, the subject 83 having the small body size can easily take the correct measurement posture when inserting the upper arm 90 into the cuff 3.

As described above, according to the sphygmomanometer 1, the subjects 81 to 83 having various body sizes can take the correct measurement postures in a short time.

(Restriction of Swing Range)

Figure 12:
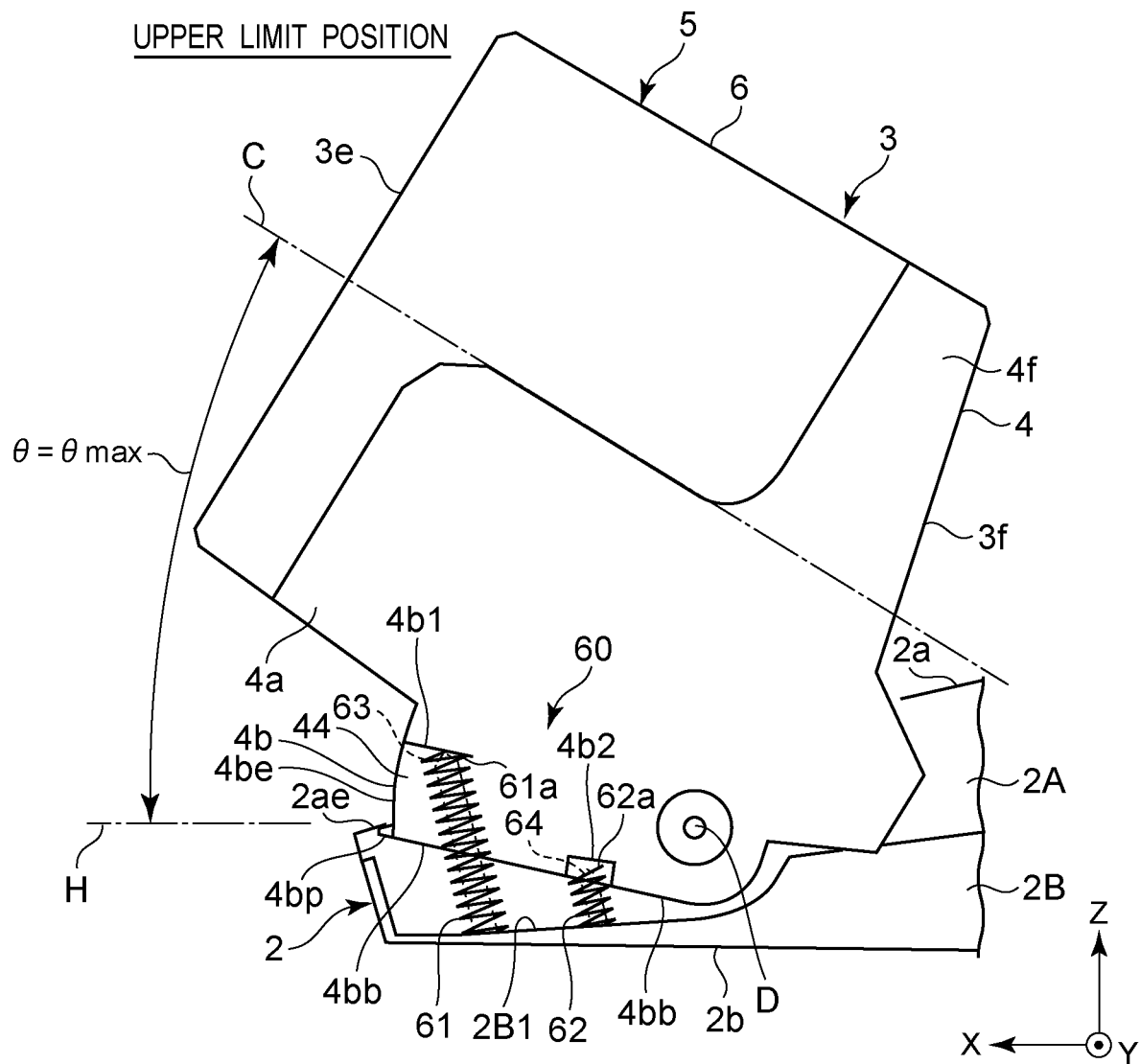
FIG. 12 is a diagram schematically showing a cross section of the cuff at an upper limit position as viewed from the right side.
Figure 13:
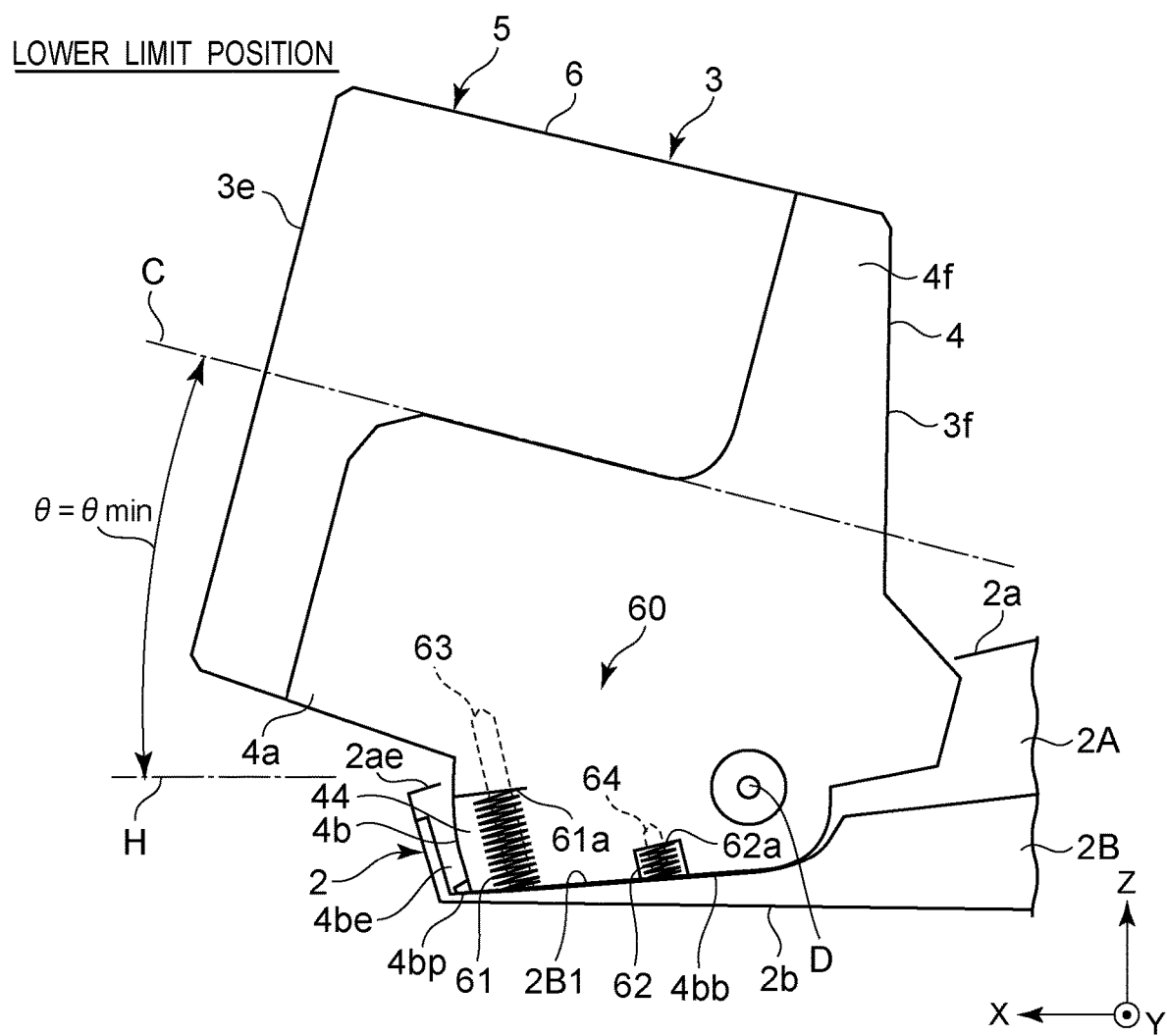
FIG. 13 is a diagram schematically showing a cross section of the cuff at a lower limit position as viewed from the right side.

In this example, a range within which the tilt angle θ of the cuff 3 can be changed is restricted to a range from an upper limit tilt angle θmax shown in FIG. 12 to a lower limit tilt angle θ min shown in FIG. 13.

Specifically, as shown in FIG. 12, the lower edge 4bb of the cuff housing lower part 4b is provided with the protrusion 4bp protruding forward. (As shown in FIG. 4, this protrusion 4bp is provided at a portion corresponding to substantially the center in the left-right direction (Y direction) of the cuff housing lower part 4b). When the tilt angle θ of the cuff 3 becomes larger than the standby angle θs and reaches a predetermined upper limit tilt angle θmax, the protrusion 4bp comes into contact with a front inner edge 2ae of the main body upper part 2A. The front inner edge 2ae of the main body upper part 2A functions as an upper stopper to restrict the tilt angle θ of the cuff 3 from exceeding the upper limit tilt angle θmax. Therefore, in FIG. 12, the cuff 3 is at the upper limit position. In this example, even at this upper limit position, the upper end 61a of the first coil spring 61 is in contact with the first portion 4b1 of the cuff 3.

On the other hand, as shown in FIG. 13, when the tilt angle θ of the cuff 3 becomes smaller than the standby angle θs and reaches a predetermined lower limit tilt angle θ min, the lower edge 4bb of the cuff housing lower part 4b abuts on the tilted plate part 2B1. The tilted plate part 2B1 functions as a lower stopper to restrict the tilt angle θ of the cuff 3 from falling below the lower limit tilt angle θ min. Therefore, in FIG. 13, the cuff 3 is at the lower limit position.

In this example, the upper limit tilt angle θmax is set in accordance with the subject assumed to have a maximum body size. The lower limit tilt angle θ min is set in accordance with the subject assumed to have minimum body size. Specifically, the upper limit tilt angle is set to θmax=32° and the lower limit tilt angle is set to θmin=15°. The above-described gentle tilt of the tilted plate part 2B1 with respect to the horizontal plane H is set to realize the lower limit tilt angle θmin=15°.

In this way, in this example, the range within which the tilt angle θ of the cuff 3 can change is restricted to the range from the upper limit tilt angle θmax shown in FIG. 12 to the lower limit tilt angle θmin shown in FIG. 13. Therefore, the tilt angle θ of the cuff 3 can be prevented from changing to fall in an unnecessary range.

(Block Configuration of Control System)

Figure 15:
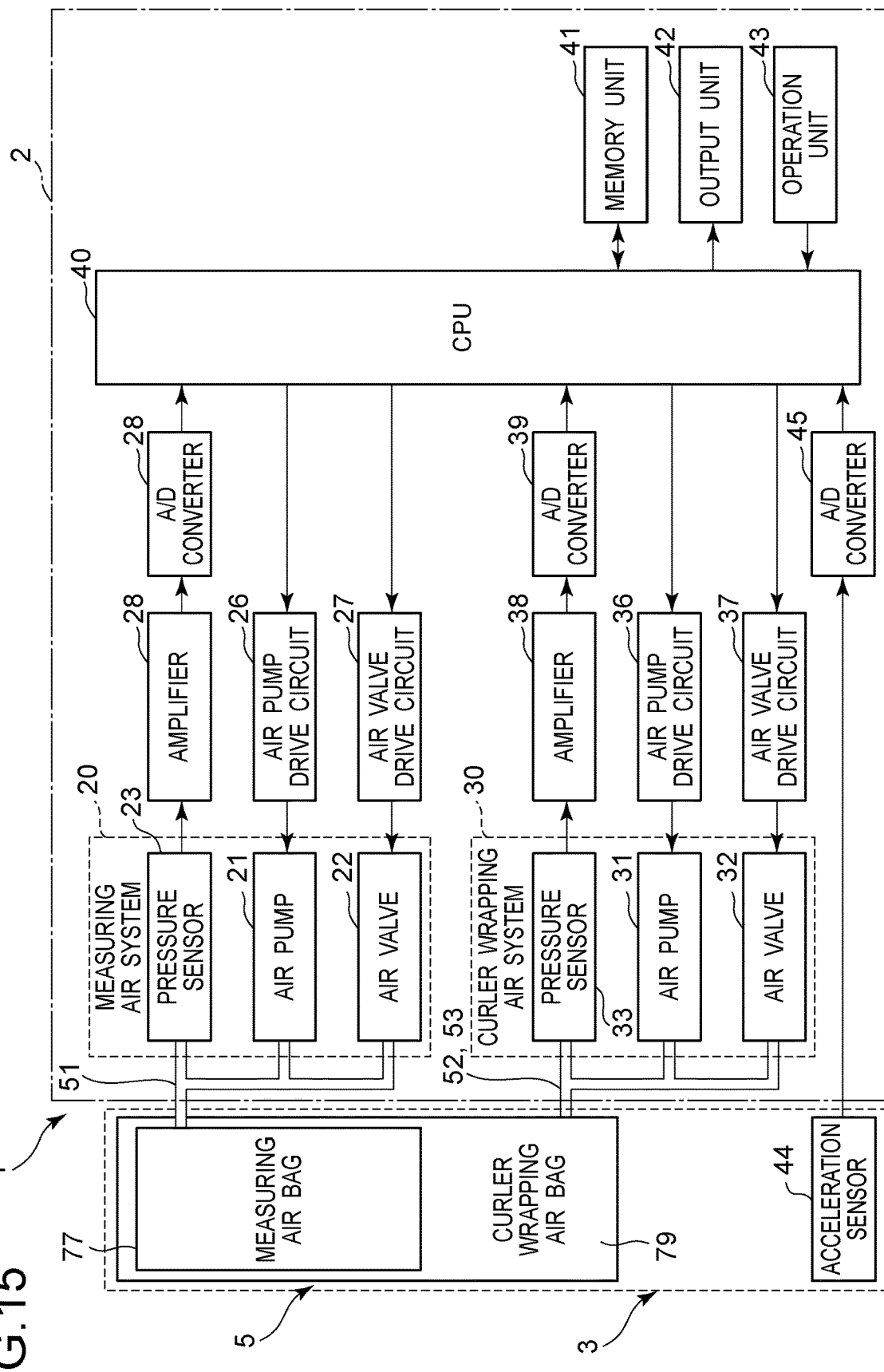
FIG. 15 is a diagram showing a block configuration of a control system of the sphygmomanometer.

FIG. 15 shows a block configuration of a control system of the sphygmomanometer 1 in a state of the cuff unit 5 being attached to the main body 2. As shown in FIG. 15, in the state of the cuff unit 5 being attached to the main body 2, the measuring air bag 77 in the cuff unit 5 is connected to a measuring air system 20 in the main body 2 via a fluid connector 51 (see FIG. 5). The curler wrapping air bag 79 in the cuff unit 5 is connected to a curler wrapping air system 30 in the main body 2 via fluid connectors 52 and 53 (see FIG. 5). The operations of the measuring air system 20 and the curler wrapping air system 30 are each controlled by a central processing unit (CPU) 40.

The measuring air system 20 includes an air pump 21, an air valve 22, and a pressure sensor 23. The air pump 21 is means for pressurizing inside of the measuring air bag 77, is driven by an air pump drive circuit 26 that receives a command from the CPU 40, and feeds the air as a fluid so that the pressure inside of the measuring air bag 77 becomes a predetermined pressure during measurement.

The air valve 22 is means for maintaining or reducing the pressure in the measuring air bag 77, and the open/closed state thereof is controlled by an air valve drive circuit 27 that receives a command from the CPU 40. The air value 22 also maintains or reduces the pressure in the measuring air bag 77 which is highly pressurized by the air pump 21 during measurement, and returns the pressure in the measuring air bag 77 to the atmospheric pressure after the measurement is completed.

The pressure sensor 23 is means for detecting the pressure in the measuring air bag 77, detects the pressure in the measuring air bag 77 that changes every moment during measurement, and outputs a signal according to the detected value to an amplifier 28. The amplifier 28 amplifies the signal output from the pressure sensor 23 and outputs the signal to an analog/digital (A/D) converter 29. The A/D converter 29 digitizes the analog signal output from the amplifier 28 and outputs the signal to the CPU 40.

The curler wrapping air system 30 includes an air pump 31, an air valve 32, and a pressure sensor 33. The air pump 31 is means for pressurizing inside of the curler wrapping air bag 79, is driven by an air pump drive circuit 36 that receives a command from the CPU 40, and feeds the air as a fluid so that the pressure inside the curler wrapping air bag 79 becomes a predetermined pressure at the start of measurement.

The air valve 32 is means for maintaining and reducing the pressure in the curler wrapping air bag 79, and the open/closed state thereof is controlled by an air valve drive circuit 37 that receives a command from the CPU 40. The air valve 32 also maintains the pressure in the curler wrapping air bag 79 which is highly pressurized by the air pump 31 during measurement, and returns the pressure in the curler wrapping air bag 79 to the atmospheric pressure after the measurement is completed.

The pressure sensor 33 is means for detecting the pressure in the curler wrapping air bag 79, detects the pressure in the curler wrapping air bag 79 at the start of measurement, and outputs a signal corresponding to the detected value to an amplifier 38.

The amplifier 38 amplifies the signal output from the pressure sensor 33 and outputs the signal to an A/D converter 39. The A/D converter 39 digitizes the analog signal output from the amplifier 38 and outputs the signal to the CPU 40.

In this example, an output unit 42 includes the display 11 described above, a printer 12, and a not-shown speaker.

In this example, an operation unit 43 includes the measurement start/stop switches 13A and 13B and the print instruction switch 14 described above.

The CPU 40 controls the measuring air system 20 and the curler wrapping air system 30 based on the command input to the operation unit 43, and outputs the measurement result to the output unit 42 and a memory unit 41. The memory unit 41 is means for storing the measurement result. Further, when the print instruction switch 14 is pressed, the CPU 40 causes the printer 12 to print out the measurement result on paper (roll paper in this example).

(Blood Pressure Measurement Operation)

FIG. 16 shows an operation flow of blood pressure measurement by the CPU 40 in the sphygmomanometer 1 configured as described above. In this example, when the subject presses the measurement start/stop switch 13A or 13B provided on the operation unit 43 of the main body 2 in the state of passing the upper arm 90 through the cuff unit 5, the operation is shifted to the measurement operation.

First, in step S1, the sphygmomanometer 1 is initialized. At this time, in the cuff unit 5 (cuff structure 7), as shown in FIG. 14A, the pressures in the measuring air bag 77 and the curler wrapping air bag 79 are both zero (atmospheric pressure). In this state (natural state), end parts of the curler 78 in the circumferential direction overlap with each other, and end parts of the measuring air bag 77 in the circumferential direction are relatively separated from each other.

Figure 14C:
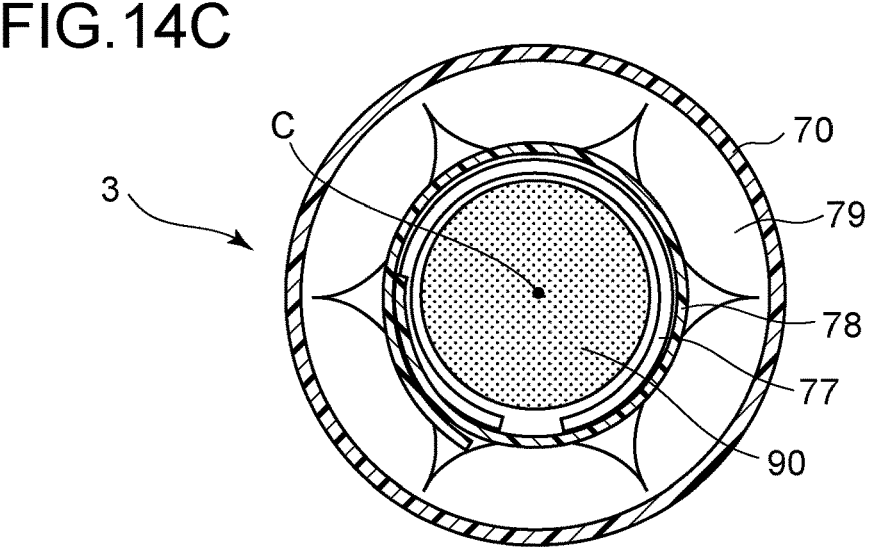

Next, in step S2 of FIG. 16, the CPU 40 acts as the pressure control unit and supplies the air from the air pump 31 to the curler wrapping air bag 79 via the fluid connectors 52 and 53. As a result, the curler wrapping air bag 79 is pressurized. At this time, in the cuff unit 5 (cuff structure 7), as shown by an arrow A11 in FIG. 148, the curler wrapping air bag 79 expands inward in the radial direction to compress the curler 78 inward in the radial direction. As a result, an overlapped dimension of the end parts of the curler 78 in the circumferential direction increases as indicated by an arrow A12, and the end parts of the measuring air bag 77 in the circumferential direction approach each other. Then, when the pressure inside the curler wrapping air bag 79 reaches a predetermined pressure, the pressurization of the curler wrapping air bag 79 is completed (step S3). As a result, as shown in FIG. 14C, the upper arm 90 is surrounded by the measuring air bag 77.

Next, in step S4 of FIG. 16, the CPU 40 acts as the pressure control unit and supplies the air from the air pump 21 to the measuring air bag 77 via the fluid connector 51. As a result, the measuring air bag 77 is pressurized. Then, when the pressure inside the measuring air bag 77 reaches a predetermined pressure, the pressurization of the measuring air bag 77 is completed, and in step S5, the depressurization of the measuring air bag 77 is started.

After that, in step S6, the CPU 40 functions as the blood pressure calculation unit, detects the arterial pressure pulse wave (pressure fluctuation component) based on the output of the pressure sensor 23, and calculates the blood pressure based on the detection data of the arterial pressure pulse wave (oscillometric method). When the calculation of the blood pressure value is completed, in step S7, the blood pressure value is displayed on the display 1 provided in the output unit 42 of the main body 2, and in step S8, the inside of the curler wrapping air bag 79 and the inside of the measuring air bag 77 are opened to the atmosphere.

Thus, according to the sphygmomanometer 1, the blood pressure can be easily measured by the subject. The blood pressure may be calculated in the pressurizing process instead of the depressurizing process.

(Arm Insertion Detection)

As shown in FIG. 15, the cuff 3 is provided with the acceleration sensor 44. As shown in FIG. 4, the acceleration sensor 44 is provided integrally with the cuff housing lower part 4b (i.e., the cuff 3) at a portion closer to the front surface side (+X side) in the cuff housing lower part 4b. The acceleration sensor 44 is configured to output acceleration components of three axes (x-axis, y-axis, and z-axis shown in FIG. 19A in this example) fixed to the acceleration sensor 44. The outputs of the three axes of the acceleration sensor 44 are digitized via the A/D converter 45 shown in FIG. 15 and input to the CPU 40. In this example, the CPU 40 functions as the arm insertion determination unit and determines whether or not the arm has been inserted into the cuff 3 based on the change in the output of the acceleration sensor 44.

Specifically, as shown in a flow of FIG. 17, the CPU 40 first detects the outputs of the three axes of the acceleration sensor 44 (step S11). The outputs of the three axes of the acceleration sensor 44 are denoted as $\alpha x$, $\alpha y$, and $\alpha z$.

Next, in step S12, the CPU 40 removes environmental noise and vibration during operation from the outputs $\alpha x$, $\alpha y$, and $\alpha z$ of the three axes via a not-shown low-pass filter. In this example, the cutoff frequency of the low-pass filter is set to 5 Hz.

Next, in step S13, the CPU 40 performs the known moving average processing on the signal filtered through the low-pass filter. The average values obtained by this moving average processing are denoted as $<\alpha x>$, $<\alpha y>$, and $<\alpha z>$.

Next, in step S14, the CPU 40 extracts a change point by performing the differentiation processing. Specifically, the CPU 40 calculates ($\alpha x-<\alpha x>$), ($\alpha y-<\alpha y>$), and ($\alpha z-<\alpha z>$) which are amounts of fluctuation that the acceleration outputs $\alpha x$, $\alpha y$, and $\alpha z$ at each time point during a unit period fluctuate with respect to the average values $<\alpha x>$, $<\alpha y>$, and $<\alpha z>$, respectively.

Figure 18A:
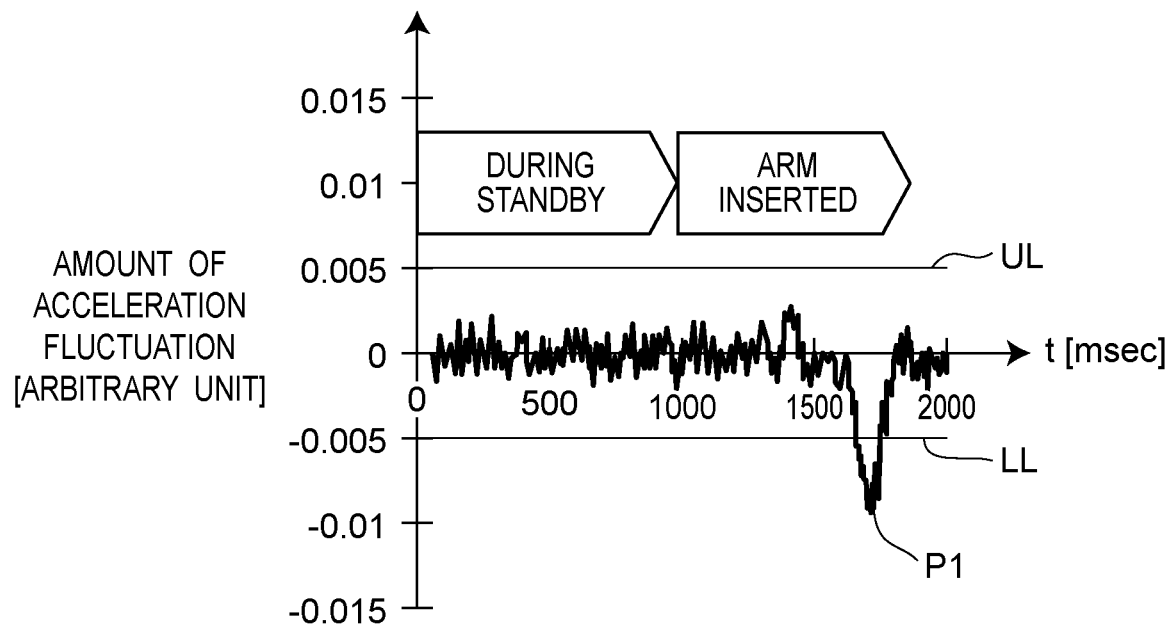
FIG. 18A and FIG. 18B are diagrams chronologically showing an amount of acceleration fluctuation output by an acceleration sensor integrally attached to the cuff.
Figure 18B:
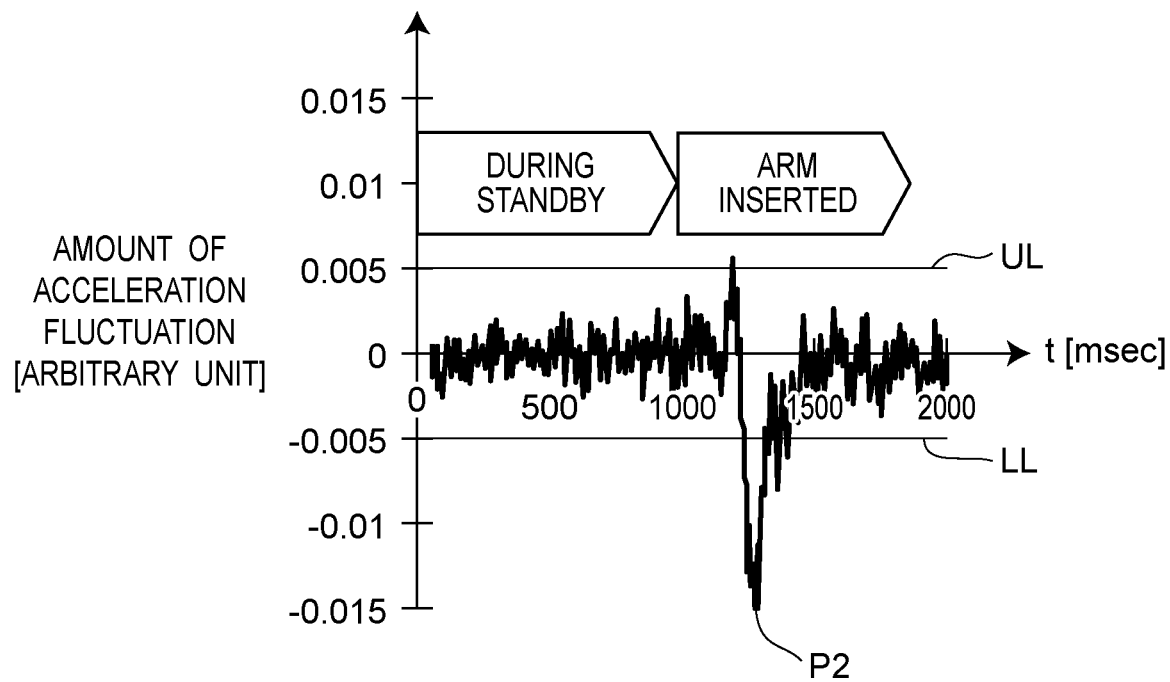

Here, FIG. 18A and FIG. 18B chronologically show the amount of acceleration fluctuation (for one component representing ($\alpha x-<\alpha x>$) in this example) output by the acceleration sensor 44. (The unit of the vertical axis is an arbitrary unit in the arithmetic processing by the CPU 40). FIG. 18A corresponds to an amount of acceleration fluctuation when the arm is slowly inserted into the cuff 3. FIG. 18B corresponds to the amount of acceleration fluctuation when the arm is normally inserted into the cuff 3. Negative peaks P1 and P2 in FIGS. 18A and 18B represent peaks due to the arm abutting on the inner circumferential surface 3i of the cuff 3. In this example, based on these FIG. 18A and FIG. 18B, for each component of the amount of acceleration fluctuation, first threshold values are set to ±0.005 (that is, a positive-side threshold value UL=+0.005, and a negative-side threshold old value LL=−0.005).

Next, in step S15 of FIG. 17, it is determined whether or not the amounts of acceleration fluctuation ($\alpha x-<\alpha x>$), ($\alpha y-<\alpha y>$), and ($\alpha z-<\alpha z>$) have exceeded the first threshold value UL or LL. (More precisely, it is determined whether the amounts have exceeded the positive-side threshold value UL or fallen below the negative-side threshold value LL). Here, if none of the amounts of acceleration fluctuation ($\alpha x-<\alpha x>$), ($\alpha y-<\alpha y>$), and ($\alpha z-<\alpha z>$) exceeds the first threshold UL or LL (NO in step S15), the CPU 40 determines that the arm is not inserted into the cuff 3, and returns to step S11 to continue the processing. On the other hand, if any of the amounts of acceleration fluctuation ($\alpha x-<\alpha x>$), ($\alpha y-<\alpha y>$), and ($\alpha z-<\alpha z>$) has exceeded the first threshold value UL or LL (YES in step S15), the CPU 40 determines that the arm has been inserted into the cuff 3 (step S16).

Therefore, based on this determination result, the CPU 40 can issue by a voice or display through the output unit 42, for example, at an appropriate timing, a guidance such as an operation method for starting measurement and a measurement posture to be taken. As a result, even if the subject is not accustomed to the operation, the correct operation can be smoothly performed, and the correct blood pressure measurement result can be obtained.

In this sphygmomanometer 1, in the standby state of the upper arm 90 not being inserted into the cuff 3, the cuff 3 is loosely supported by the swing mechanism 60, and the tilt angle θ of the cuff 3 can be easily changed from the standby angle θs to the larger or smaller angle. Therefore, the accuracy of the arm insertion detection by the acceleration sensor 44 can be improved. Further, because the acceleration sensor 44 is provided in the portion closer to the front surface side (+X side) in the cuff housing lower part 4b, when the arm is inserted into the cuff 3, the movement is more significant than in a portion near the rotating shaft D. Therefore, the accuracy of the arm insertion detection by the acceleration sensor 44 can be further improved.

In the above example, the first threshold values UL and LL are defined for each component of the amount of acceleration fluctuation ($\alpha x-<\alpha x>$), ($\alpha y-<\alpha y>$), and ($\alpha z-<\alpha z>$); however, the first threshold values are not limited to this. For example, the square root of the sum of squares of the amount of acceleration fluctuation, represented by $\{(\alpha x-<\alpha x>)^2-(\alpha y-<\alpha y>)^2+(\alpha z-<\alpha z>)^2\}^{1/2}$, is calculated, and the first threshold values may be set for this square root of the sum of squares. Then, it may be determined whether or not the arm has been inserted into the cuff 3, depending on whether or not the square root of the sum of squares exceeds the first threshold values.

(Lower Part Compression Determination)

Figure 19A:
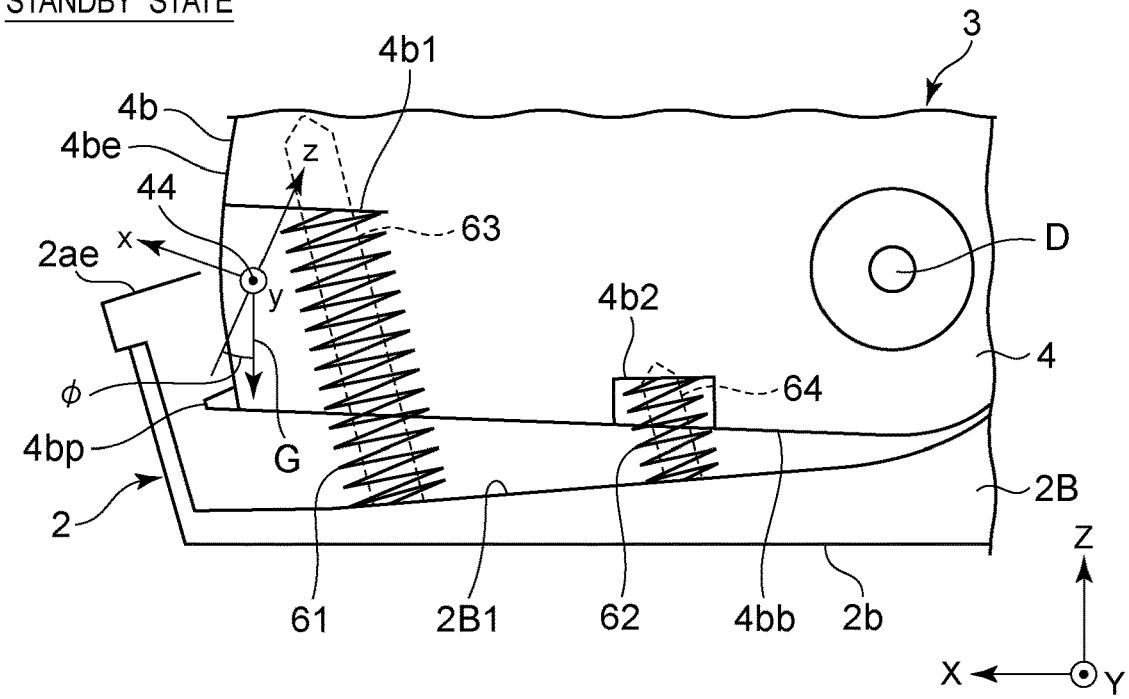
FIG. 19A is a diagram schematically showing a cross section of the cuff in a state of being at a standby angle, as viewed from the right side and including the xyz orthogonal coordinate system fixed to the acceleration sensor.
Figure 19B:
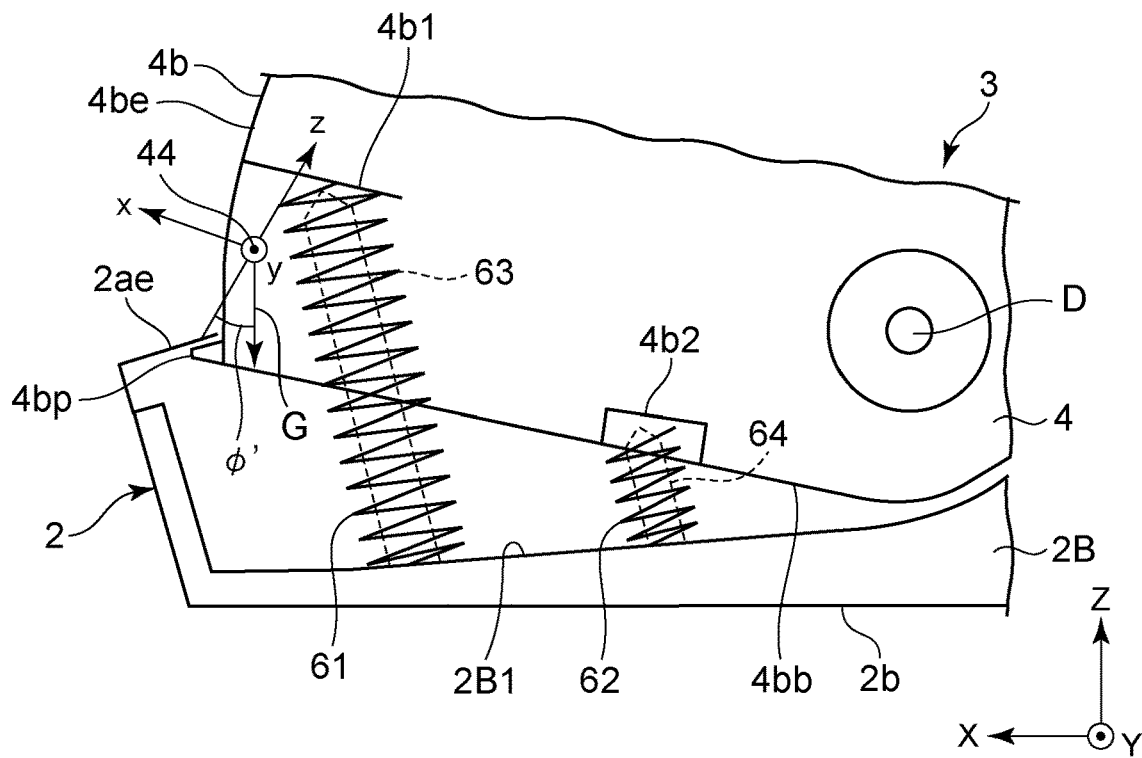
FIG. 19B is a diagram schematically showing a cross section of the cuff in the state of being at the upper limit position, as viewed from the right side and including the xyz orthogonal coordinate system fixed to the acceleration sensor.
Figure 19C:
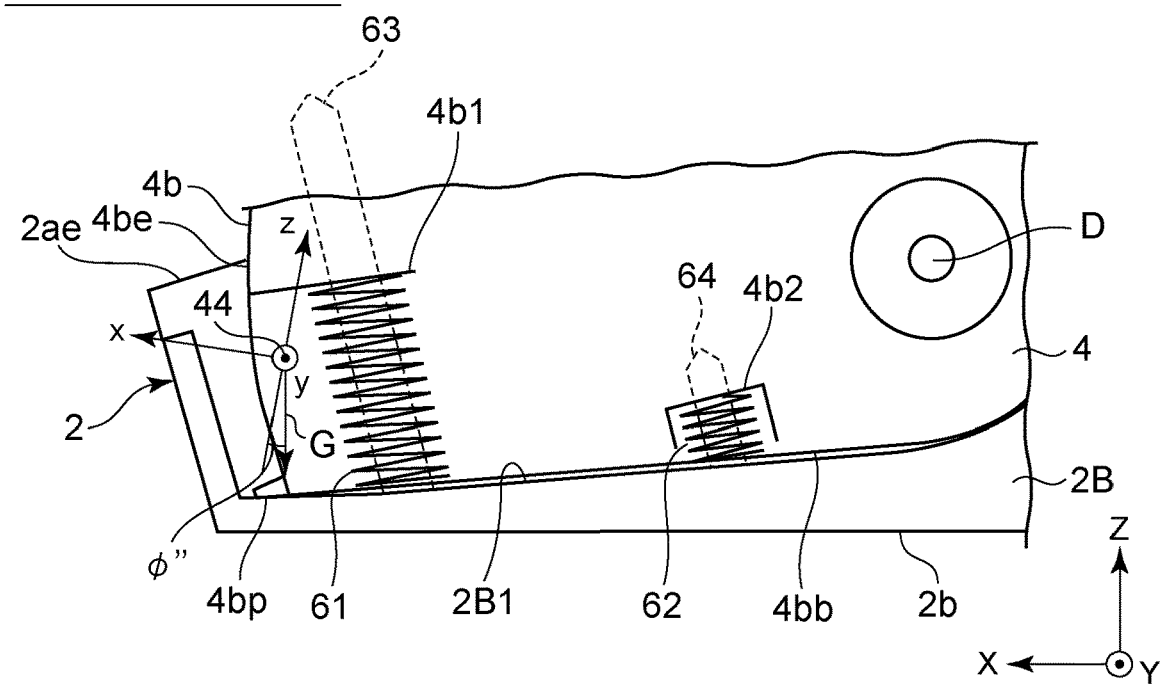
FIG. 19C is a diagram schematically showing a cross section of the cuff in the state of being at the lower limit position, as viewed from the right side and including the xyz orthogonal coordinate system fixed to the acceleration sensor.

As described above, the acceleration sensor 44 is configured to output the acceleration components of the three axes (x-axis, y-axis, and z-axis shown in FIG. 19A in this example) fixed to the acceleration sensor 44. The x-axis is oriented in the front-back direction, the y-axis is oriented in the left-right direction, and the z-axis is oriented in the up-down direction (vertical direction) substantially. With the swing of the cuff 3, the orientations of the three axes (xyz orthogonal coordinate system) with respect to the XYZ orthogonal coordinate system, particularly the orientation of the z-axis with respect to the Z-axis (that is, the direction of a gravity acceleration vector G) changes. For example, as shown in FIG. 19A, when the cuff 3 is in the standby state, it is assumed that an angle of the z-axis of the acceleration sensor 44 with respect to the gravitational acceleration vector G is φ. At this time, a component of the gravitational acceleration output from the z-axis of the acceleration sensor 44 is approximately G cos φ. As shown in FIG. 19B, when the cuff 3 is at the upper limit position, the angle of the z-axis of the acceleration sensor 44 with respect to the gravitational acceleration vector G is φ'(>φ). At this time, the component of the gravitational acceleration output from the z-axis of the acceleration sensor 44 is approximately G cos φ' (<G cos φ). Conversely, as shown in FIG. 19C, when the cuff 3 is at the lower limit position, the angle of the z-axis of the acceleration sensor 44 with respect to the gravitational acceleration vector G is φ" (<φ). At this time, the component of the gravitational acceleration output from the z-axis of the acceleration sensor 44 is approximately G cos φ" (>G cos φ). Therefore, in this example, the CPU 40 functions as the lower part compression determination unit, and based on the component of the gravity acceleration vector G output by the z-axis of the acceleration sensor 44, it is determined whether or not the cuff 3 is in a state of being pressed downward (lower part compressed state).

Figure 20:
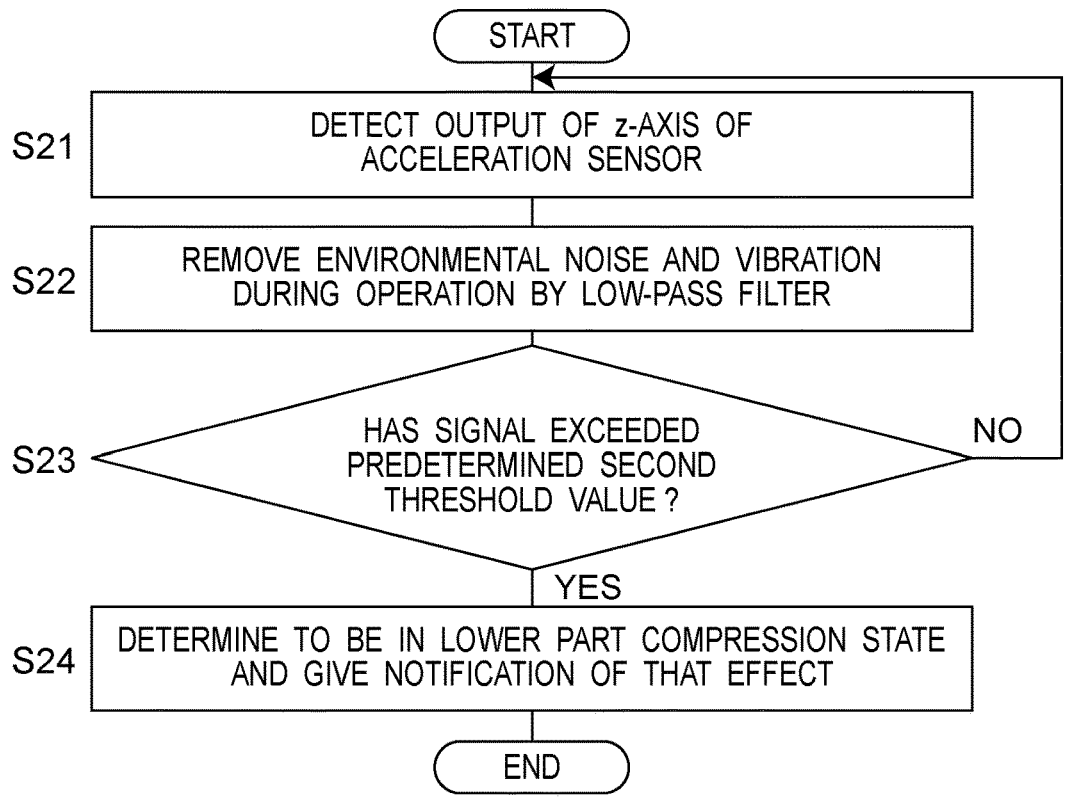
FIG. 20 is a diagram showing a flow for detecting that the cuff is in a lower part compressed state in the sphygmomanometer.

Specifically, as shown in the flow of FIG. 20, first, the CPU 40 detects the output of the acceleration sensor 44 in the z-axis (step S21). The z-axis output of the acceleration sensor 44 is denoted as αz.

Next, in step S22, the CPU 40 removes environmental noise and vibration during operation from the z-axis output αz via a not-shown low-pass filter. In this example, the cutoff frequency of the low-pass filter is set to 5 Hz.

Figure 21:
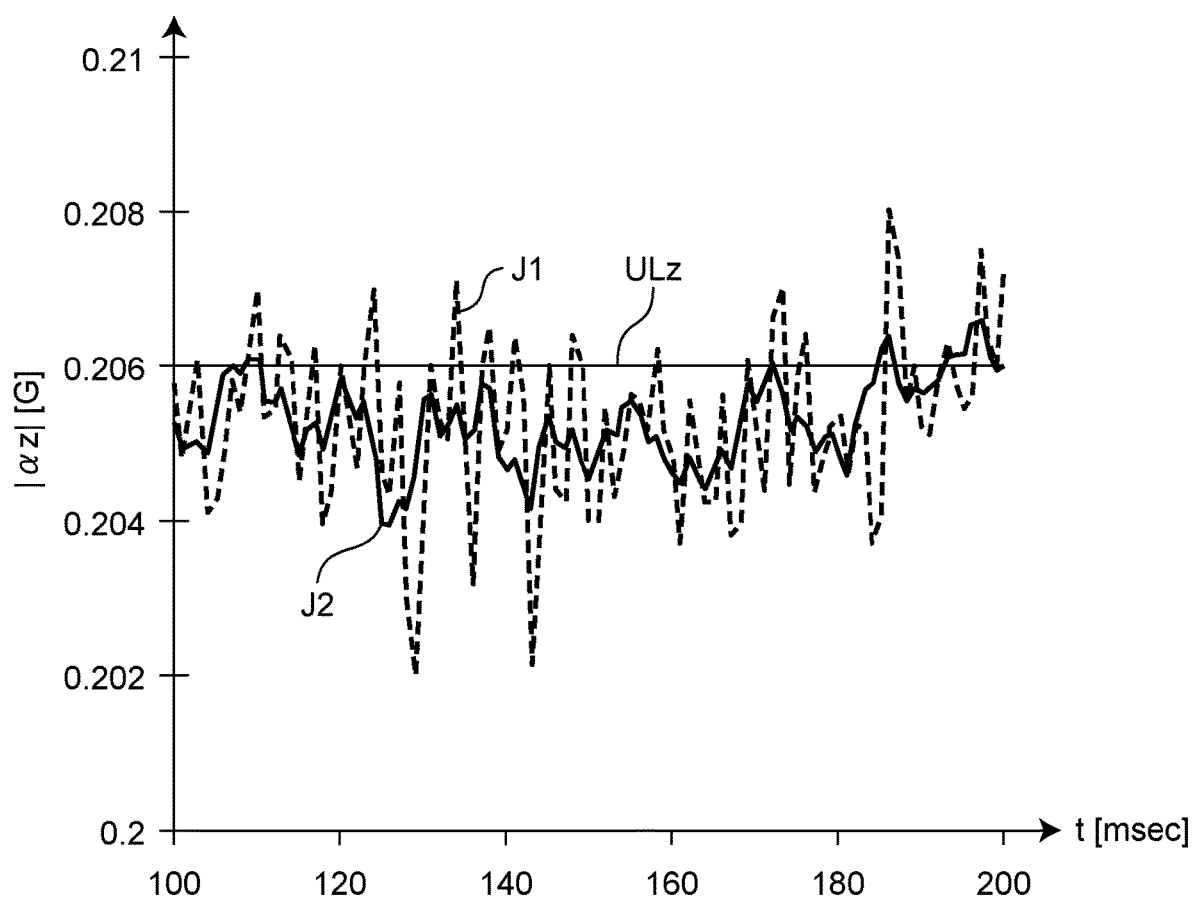
FIG. 21 is a diagram chronologically showing a component (component of a gravitational acceleration vector) output from the z-axis of the acceleration sensor.

Here, a broken line J1 in FIG. 21 chronologically shows a signal (represented by an absolute value |αz| for simplicity) filtered through the low-pass filter when the cuff 3 is at the lower limit position as shown in FIG. 19C. In this example, based on FIG. 21, a second threshold value ULz is set to 0.206 for the filtered signal |αz"|.

Next, in step S23 of FIG. 20, the CPU 40 determines whether or not the filtered signal |αz| exceeds the second threshold value ULz. Here, if the filtered signal |αz| does not exceed the second threshold ULz (NO in step S23), the CPU 40 determines that the cuff 3 is not pressed downward, and returns to step S21 to continue the processing. On the other hand, if the filtered signal |αz| exceeds the second threshold ULz (YES in step S23), the CPU 40 determines that the cuff 3 is in the lower part compressed state in which the cuff 3 is pressed downward, and gives notification of that effect (step S24). In this example, the CPU 40 outputs a voice or display through the output unit 42 that the cuff 3 is in the lower part compressed state.

From the notification, the subject comes to know that one is in the lower part compressed state, and can take necessary measures such as laying a cushion under the hip to make the position of one's shoulder higher.

In the above example, the second threshold value ULz is directly set for the signal |αz| filtered through the low-pass filter; however, the present invention is not limited to this. For example, the known moving average processing may be performed on the filtered signal |αz|, and a second threshold value may be set for an average value <|αz|> obtained by this moving average processing. For example, a broken line J2 in FIG. 21 indicates the average value <|αz|> obtained by this moving average processing. Depending on whether or not the average value <αz|> obtained by the moving average processing exceeds the second threshold value, it may be determined whether or not the cuff 3 is in the lower part compressed state.

The cutoff frequency of the low-pass filter, the first threshold values UL and LL, and the second threshold value ULz are preferably determined according to the environment in which the sphygmomanometer 1 is installed.

In this embodiment, the cuff 3 is constituted of the cuff housing 4 and the cuff unit 5 detachably attached to the cuff housing 4. However, the configuration is not limited to this. The cuff housing 4 of the cuff 3 and the cuff unit 5 may be integrally constituted in a non-detachable manner.

Further, in this embodiment, the cuff unit 5 is configured such that the base member 70 includes the curler wrapping air bag 79, the curler 78, and the measuring air bag 77; however, the present invention is not limited to this. The curler wrapping air bag 79 and the curler 78 may be omitted, and only the measuring air bag 77 may compress the measurement target site.

In this embodiment, the measurement target site inserted into the cuff unit 5 is the upper arm 90; however, the measurement target site is not limited to this. The measurement target site may be a wrist, a finger, a lower limb, or others.

As described above, a sphygmomanometer of the present disclosure comprises:
 a main body; and
 a cuff having a cylindrical shape, rotatably attached to the main body about a rotating shaft horizontal to the main body, and into which an upper arm of a subject is inserted,
 wherein the cuff has a fluid bag configured to compress the upper arm of the subject along an inner circumferential surface of the cuff, and is attached to the rotating shaft on a rear surface side opposite to a front surface side arranged facing the subject during blood pressure measurement, in a direction in which a central axis of the cuff extends, and
 wherein the sphygmomanometer further comprises a swing mechanism configured to maintain, in a standby state of the upper arm not being inserted into the cuff, a tilt angle of the central axis of the cuff with respect to a horizontal plane at a standby angle at which the front surface side is higher than the rear surface side, and by the upper arm being inserted into the cuff, allow the tilt angle of the central axis of the cuff with respect to the horizontal plane to become either larger or smaller than the standby angle, and
 wherein the swing mechanism includes:
 a first coil spring erected at a position in the main body facing a first portion on the front surface side of the cuff; and
 a second coil spring erected at a position in the main body facing a second portion between the first portion and the rotating shaft in a front-back direction,
 wherein the first coil spring has a length in a natural state longer than a length of the second coil spring in the natural state, and the first coil spring has a spring constant set smaller than a spring constant of the second coil spring, and
 wherein, in the standby state, by the first portion of the cuff compressing the first coil spring from the natural length by a weight of the cuff and the second portion of the cuff abutting on an upper end of the second coil spring, the tilt angle of the central axis of the cuff with respect to the horizontal plane is maintained at the standby angle.

As used herein, the "main body" may be, for example, a main body accommodating a pump or a part thereof (e.g., a main body lower part).

Further, the phrase the cuff is "attached" to the main body includes not only the case of the cuff being attached non-detachably but also the case of the cuff being attached detachably.

The "tubular" of the "tubular cuff" is typically cylindrical, but the cross section of the outer circumferential surface of the cuff may be polygonal or any other shape.

Further, the "standby angle" is typically set in accordance with a subject having a standard body size. Generally, for a subject having a large body size, the appropriate tilt angle of the cuff with respect to the horizontal plane (main body) is large, and for a subject having a small body size, the appropriate tilt angle of the cuff with respect to the horizontal plane (main body) is small (see, for example, Japanese Patent No. 5287572).

In the sphygmomanometer of the present disclosure, in the standby state in which the upper arm is not inserted into the cuff, the swing mechanism maintains the tilt angle of the central axis of the cuff with respect to the horizontal plane (hereinafter, simply referred to as "the tilt angle of the cuff") at a certain standby angle such that the front surface side is higher than the rear surface side. At the same time, the swing mechanism allows the tilt angle of the cuff to become either larger or smaller than the standby angle by the upper arm being inserted into the cuff. Therefore, according to the sphygmomanometer of the present disclosure, the subjects having various body sizes can easily insert the upper arms into the cuff.

In addition, the "standby angle" can be set in accordance with a subject having a standard body size. In this case, if the subject has a standard body size, an angular difference for rotating the tilt angle of the cuff to an appropriate angle suitable for one's body size is substantially zero. Therefore, the subject does not have to find the tilt angle of the cuff. As a result, the subject having the standard body size can take the correct measurement posture in a short time when inserting the upper arm into the cuff.

In the case of a subject having the large body size, generally, the appropriate tilt angle of the cuff with respect to the horizontal plane (main body) becomes large. In the above case, because the upper arm pushes the inner circumferential surface of the cuff upward by inserting the upper arm into the cuff, the tilt angle of the cuff tends to become larger than the standby angle. Here, the swing mechanism allows the tilt angle of the cuff to become larger than the standby angle. Therefore, the tilt angle of the cuff becomes large to follow the body size of the subject, and the subject does not need to find the tilt angle of the cuff. As a result, the subject having the large body size can take the correct measurement posture in a short time when inserting the upper arm into the cuff.

On the other hand, in the case of a subject having the small body size, generally, the appropriate tilt angle of the cuff with respect to the horizontal plane (main body) becomes small. In the above case, because the upper arm pushes the inner circumferential surface of the cuff downward by inserting the upper arm into the cuff, the tilt angle of the cuff tends to become smaller than the standby angle. Here, the swing mechanism allows the tilt angle of the cuff to become smaller than the standby angle. Therefore, the tilt angle of the cuff become small to follow the body size of the subject, and the subject does not need to find the tilt angle of the cuff. As a result, the subject having the small body size can take the correct measurement posture in a short time when inserting the upper arm into the cuff.

As described above, according to the sphygmomanometer of the present disclosure, the subjects having various body sizes can take the correct measurement postures in a short time.

In the present description, the phrase the first coil spring and the second coil spring are "erected" on the main body means that the coil spring is provided in a state in which the expansion and contraction direction of the coil spring is substantially vertical or nearly substantially vertical.

Especially, in the sphygmomanometer, the swing mechanism operates as follows. That is, in the standby state, the first portion of the cuff compresses the first coil spring from its natural length by the weight of the cuff. Here, because the spring constant of the first coil spring is set relatively small (smaller than the spring constant of the second coil spring), the first coil spring is easily compressed from the natural length and shortened in length. As a result, the second portion of the cuff comes into contact with the upper end of the second coil spring. Here, because the spring constant of the second coil spring is set relatively large (larger than the spring constant of the first coil spring), the second coil spring supports the weight of the cuff by elastic force of the first coil spring and elastic force of the second coil spring, only by becoming slightly shorter than the natural length. Thereby, the tilt angle of the central axis of the cuff with respect to the horizontal plane is maintained at the standby angle.

In the case of the subject having the large body size, as described above, because the upper arm pushes the inner circumferential surface of the cuff upward by the upper arm being inserted into the cuff, the tilt angle of the cuff tends to become larger than the standby angle. When the tilt angle of the cuff tends to become larger than the standby angle, the first coil spring expands as the height of the first portion of the cuff increases. Further, as the height of the second portion of the cuff increases, the second coil spring also slightly expands, and when the height of the second portion increases to a certain extent, the upper end of the second coil spring is separated from the second portion. In this way, the tilt angle of the cuff is allowed to become larger than the standby angle. At this time, the first coil spring pushes the first portion of the cuff upward by the elastic force while expanding. Therefore, the force required for the upper arm of the subject to push the inner circumferential surface of the cuff upward only needs to be small. Therefore, the subject having the large body size can easily take the correct measurement posture when inserting the upper arm into the cuff.

On the other hand, in the case of the subject having the small body size, as described above, because the upper arm pushes the inner circumferential surface of the cuff downward by the upper arm being inserted into the cuff, the tilt angle of the cuff tends to become smaller than the standby angle. When the tilt angle of the cuff tends to become smaller than the standby angle by the upper arm being inserted into the cuff, the first coil spring contracts as the height of the first portion of the cuff decreases. Further, as the height of the second portion of the cuff decreases, the second coil spring also contracts. In this way, the tilt angle of the cuff is allowed to become smaller than the standby angle. At this time, the force with which the upper arm of the subject pushes the inner circumferential surface of the cuff downward is mainly due to the body weight, and therefore, the burden on the upper arm of the subject is small. Therefore, the subject having the small body size can easily take the correct measuring posture when inserting the upper arm into the cuff.

The swing mechanism can be simply configured substantially by adding two members which are the first coil spring and the second coil spring.

In the sphygmomanometer of one embodiment, the first coil spring and the second coil spring are fitted around a first mandrel and a second mandrel that are erected at positions corresponding to the first coil spring and the second coil spring of the main body, respectively, and wherein the first portion and the second portion of the cuff are provided with a first relief part and a second relief part, respectively, the first relief part and the second relief part allowing the first mandrel and the second mandrel to pass as the cuff rotates about the rotating shaft.

In the sphygmomanometer of the one embodiment, the first coil spring and the second coil spring are erected on the main body while being fitted around the first mandrel and the second mandrel, respectively. Therefore, even if the compression and expansion of the first coil spring and the second coil spring are repeated as the sphygmomanometer is used, the first coil spring and the second coil spring are firmly and stably held at the erected positions in the main body. Further, the first portion and the second portion of the cuff are provided with the first relief part and the second relief part, respectively, each of which allows the first mandrel and the second mandrel to pass therethrough as the cuff rotates about the rotating shaft. Therefore, the first mandrel and the second mandrel do not interfere with the first portion and the second portion of the cuff. The first mandrel and the second mandrel may be integrally formed with the main body by, for example, integral molding. In this case, the first mandrel and the second mandrel do not become a cause of increase in the number of members of the swing mechanism.

In the sphygmomanometer of one embodiment, the sphygmomanometer comprises:
  an upper stopper that restricts the tilt angle of the central axis of the cuff with respect to the horizontal plane from exceeding a predetermined upper limit tilt angle when the tile angle becomes larger than the standby angle; and
  a lower stopper that restricts the tilt angle of the central axis of the cuff with respect to the horizontal plane from falling below a predetermined lower limit tilt angle when the tilt angle becomes smaller than the standby angle.

Here, the "upper limit tilt angle" is typically set in accordance with a subject assumed to have the maximum body size. The "lower limit tilt angle" is typically set in accordance with a subject assumed to have the minimum body size.

In the sphygmomanometer according to the one embodiment, the upper stopper restricts the tilt angle of the cuff from exceeding a predetermined upper limit tilt angle when the angle becomes larger than the standby angle. Further, the lower stopper restricts the tilt angle of the cuff from falling below a predetermined lower limit tilt angle when the angle becomes smaller than the standby angle. Therefore, the tilt angle of the cuff can be prevented from changing to fall in an unnecessary range.

In another aspect, a sphygmomanometer of the present disclosure comprises:
  a main body; and
  a cuff having a cylindrical shape, rotatably attached to the main body about a rotating shaft horizontal to the main body, and into which an upper arm of a subject is inserted,
  wherein the cuff has a fluid bag configured to compress the upper arm of the subject along an inner circumferential surface of the cuff, and is attached to the rotating shaft on a rear surface side opposite to a front surface side arranged facing the subject during blood pressure measurement, in a direction in which a central axis of the cuff extends, and
  wherein the sphygmomanometer further comprises a swing mechanism configured to maintain, in a standby state of the upper arm not being inserted into the cuff, a tilt angle of the central axis of the cuff with respect to a horizontal plane at a standby angle at which the front surface side is higher than the rear surface side, and by the upper arm being inserted into the cuff allow the tilt angle of the central axis of the cuff with respect to the horizontal plane to become either larger or smaller than the standby angle, and
  wherein the sphygmomanometer further comprises:
  an acceleration sensor integrally attached to the cuff, and
  an arm insertion determination unit that determines, based on a change in an output of the acceleration sensor, whether or not an arm has been inserted into the cuff.

According to the sphygmomanometer of the present disclosure, as described above, the subjects having various body sizes can take the correct measurement postures in a short time. Furthermore, in the sphygmomanometer, the arm insertion determination unit determines whether or not the arm has been inserted into the cuff based on the change in output of the acceleration sensor integrally attached to the cuff. Therefore, based on this determination result, for example, at an appropriate timing, a guidance such as an operation method for starting measurement and a measurement posture to be taken can be issued by a voice or display. As a result, even if the subject is not accustomed to the operation, the correct operation can be smoothly performed, and the correct blood pressure measurement result can be obtained. Further, in this sphygmomanometer, in the standby state of the upper arm not being inserted into the cuff, the cuff is loosely supported by the swing mechanism, and the tilt angle of the cuff may change from the standby angle to either the large or smaller angle. Therefore, the accuracy of detecting the arm insertion by the acceleration sensor can be improved.

In the sphygmomanometer of one embodiment, the sphygmomanometer comprises:
  an acceleration sensor integrally attached to the cuff; and
  a lower part compression determination unit that determines, based on a component of a gravitational acceleration vector output by the acceleration sensor, whether or not the cuff is in a state of being pressed downward.

In the sphygmomanometer according to the one embodiment, the lower part compression determination unit determines whether or not the cuff is in a state of being pressed downward (this is referred to as a "lower part compressed state") based on a gravitational acceleration vector output by the acceleration sensor. Therefore, based on this determination result, for example, a notification can be made that the cuff is in the lower part compressed state of being pressed downward. From the notification, the subject comes to know that one is in the lower part compressed state, and can take necessary measures such as laying a cushion under the hip to make the position of one's shoulder higher.

In the sphygmomanometer of one embodiment, the main body includes:
  a pump;

a pressure control unit that supplies a fluid from the pump to the fluid bag of the cuff, and performs control to compress a measurement target site inserted into the cuff; and a blood pressure calculation unit that calculates blood pressure based on a pressure of the fluid.

In the sphygmomanometer of the one embodiment, during blood pressure measurement, the pressure control unit performs control of supplying a fluid from the pump mounted on the main body to the fluid bag to compress a measurement target site inserted into the cuff. In the process of pressurizing or depressurizing the cuff body (fluid bag), a blood pressure calculation unit calculates blood pressure based on the pressure of the fluid (oscillometric method). Therefore, the blood pressure can be easily measured by the subject.

The above embodiments are exemplifications, and various modifications can be made without departing from the scope of the present invention. The plurality of embodiments described above can be independently established, but the embodiments can be combined with each other. Further, although various features in different embodiments can be established independently, it is also possible to combine features in different embodiments.

The invention claimed is:

1. A sphygmomanometer comprising:

a main body; and a cuff having a cylindrical shape, rotatably attached to the main body about a rotating shaft horizontal to the main body, and configured to receive an upper arm of a subject when the upper arm is inserted therein, wherein the cuff has a fluid bag configured to compress the upper arm of the subject along an inner circumferential surface of the cuff, and is attached to the rotating shaft on a rear surface side opposite to a front surface side arranged facing the subject during blood pressure measurement, in a direction in which a central axis of the cuff extends, and wherein the sphygmomanometer further comprises a swing mechanism configured to maintain, in a standby state of the upper arm not being inserted into the cuff, a tilt angle of the central axis of the cuff with respect to a horizontal plane at a standby angle at which the front surface side is higher than the rear surface side, and by the upper arm being inserted into the cuff, allow the tilt angle of the central axis of the cuff with respect to the horizontal plane to become either larger or smaller than the standby angle, and wherein the swing mechanism includes:

a first coil spring erected at a position in the main body facing a first portion on the front surface side of the cuff; and a second coil spring erected at a position in the main body facing a second portion between the first portion and the rotating shaft in a front-back direction, wherein the first coil spring has a length in a natural state longer than a length of the second coil spring in the natural state, and the first coil spring has a spring constant set smaller than a spring constant of the second coil spring, and wherein, in the standby state, by the first portion of the cuff compressing the first coil spring from the natural length by a weight of the cuff and the second portion of the cuff abutting on an upper end of the second coil spring, the tilt angle of the central axis of the cuff with respect to the horizontal plane is maintained at the standby angle.

2. The sphygmomanometer according to claim 1, wherein the first coil spring and the second coil spring are fitted around a first mandrel and a second mandrel that are erected at positions corresponding to the first coil spring and the second coil spring of the main body, respectively, and wherein the first portion and the second portion of the cuff are provided with a first relief part and a second relief part, respectively, the first relief part and the second relief part allowing the first mandrel and the second mandrel to pass as the cuff rotates about the rotating shaft.

3. The sphygmomanometer according to claim 1, comprising:

an upper stopper that restricts the tilt angle of the central axis of the cuff with respect to the horizontal plane from exceeding a predetermined upper limit tilt angle when the tile angle becomes larger than the standby angle; and a lower stopper that restricts the tilt angle of the central axis of the cuff with respect to the horizontal plane from falling below a predetermined lower limit tilt angle when the tilt angle becomes smaller than the standby angle.

4. The sphygmomanometer according to claim 1, wherein the sphygmomanometer further comprises:

an acceleration sensor integrally attached to the cuff, and an arm insertion determination unit that determines, based on a change in an output of the acceleration sensor, whether or not an arm has been inserted into the cuff.

5. The sphygmomanometer according to claim 1, further comprising:

an acceleration sensor integrally attached to the cuff; and a lower part compression determination unit that determines, based on a component of a gravitational acceleration vector output by the acceleration sensor, whether or not the cuff is in a state of being pressed downward.

6. The sphygmomanometer according to claim 1, wherein the main body includes:

a pump;

a pressure control unit that supplies a fluid from the pump to the fluid bag of the cuff, and performs control to compress a measurement target site inserted into the cuff; and a blood pressure calculation unit that calculates blood pressure based on a pressure of the fluid.

\* \* \* \* \*